US011634716B2

(12) United States Patent
St. Hilaire

(10) Patent No.: US 11,634,716 B2
(45) Date of Patent: Apr. 25, 2023

(54) GENETICALLY MODIFIED MESENCHYMAL STEM CELLS FOR USE IN CARDIOVASCULAR PROSTHETICS

(71) Applicant: University of Pittsburgh—Of the Commonwealth System of Higher Education, Pittsburgh, PA (US)

(72) Inventor: Cynthia St. Hilaire, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 203 days.

(21) Appl. No.: 16/755,717

(22) PCT Filed: Oct. 15, 2018

(86) PCT No.: PCT/US2018/055908
§ 371 (c)(1),
(2) Date: Apr. 13, 2020

(87) PCT Pub. No.: WO2019/079195
PCT Pub. Date: Apr. 25, 2019

(65) Prior Publication Data

US 2021/0403915 A1 Dec. 30, 2021

Related U.S. Application Data

(60) Provisional application No. 62/572,709, filed on Oct. 16, 2017.

(51) Int. Cl.
*C12N 15/113* (2010.01)
*C12N 5/0775* (2010.01)
(Continued)

(52) U.S. Cl.
CPC ...... *C12N 15/1137* (2013.01); *A61L 27/3834* (2013.01); *C12N 5/0662* (2013.01); *C12N 15/86* (2013.01); *C12N 2310/14* (2013.01)

(58) Field of Classification Search
CPC . A61L 27/3834; A61K 35/28; C12N 2310/14; C12N 15/1137
See application file for complete search history.

(56) References Cited

U.S. PATENT DOCUMENTS 4,902,508 A 2/1990 Badylak et al.
4,956,178 A 9/1990 Badylak et al.
(Continued)

FOREIGN PATENT DOCUMENTS

WO 0116312 A2 3/2001
WO 2015143310 A1 9/2015
WO 2016138416 A1 9/2016

OTHER PUBLICATIONS

Cuevas et al. (ABSTRACT 15843, Circulation, 2020, vol. 142, Issue Suppl_3).*
(Continued)

*Primary Examiner* — Terra C Gibbs
(74) *Attorney, Agent, or Firm* — The Webb law Firm

(57) ABSTRACT

A cardiovascular graft is provided, such as a prosthetic heart valve or blood vessel, that comprises mesenchymal stem cells (MSCs) and/or progeny thereof, modified to knock down or knockout expression of the telomerases reverse transcriptase gene (TERT), or otherwise reduce activity of TERT. Also provided are a method of making the cardiovascular graft, and a method of implanting the cardiovascular graft.

22 Claims, 14 Drawing Sheets

Specification includes a Sequence Listing.

210 236 235 222 234 225 230 236 220

(51) Int. Cl.
*A61L 27/38* (2006.01)
*C12N 15/86* (2006.01)

(56) References Cited

U.S. PATENT DOCUMENTS

| | | | |
|---|---|---|---|
| 5,281,422 | A | 1/1994 | Badylak et al. |
| 5,352,463 | A | 10/1994 | Badylak et al. |
| 5,372,821 | A | 12/1994 | Badylak et al. |
| 5,554,389 | A | 9/1996 | Badylak et al. |
| 5,573,784 | A | 11/1996 | Badylak et al. |
| 5,645,860 | A | 7/1997 | Knapp, Jr. et al. |
| 5,711,969 | A | 1/1998 | Patel et al. |
| 5,753,267 | A | 5/1998 | Badylak et al. |
| 5,762,966 | A | 6/1998 | Knapp, Jr. et al. |
| 5,866,414 | A | 2/1999 | Badylak et al. |
| 6,099,567 | A | 8/2000 | Badylak et al. |
| 6,387,369 | B1 | 5/2002 | Pittenger et al. |
| 6,485,723 | B1 | 11/2002 | Badylak et al. |
| 6,576,265 | B1 | 6/2003 | Spievack |
| 6,579,538 | B1 | 6/2003 | Spievack |
| 6,696,270 | B2 | 2/2004 | Badylak et al. |
| 6,783,776 | B2 | 8/2004 | Spievack |
| 6,793,939 | B2 | 9/2004 | Badylak |
| 6,849,273 | B2 | 2/2005 | Spievack |
| 6,852,339 | B2 | 2/2005 | Spievack |
| 6,861,074 | B2 | 3/2005 | Spievack |
| 6,887,495 | B2 | 5/2005 | Spievack |
| 6,890,562 | B2 | 5/2005 | Spievack |
| 6,890,563 | B2 | 5/2005 | Spievack |
| 6,890,564 | B2 | 5/2005 | Spievack |
| 6,893,666 | B2 | 5/2005 | Spievack |
| 8,361,503 | B2 | 1/2013 | Badylak et al. |
| 8,535,719 | B2 | 9/2013 | Badylak et al. |
| 8,691,276 | B2 | 4/2014 | Badylak et al. |
| 9,237,945 | B2 | 1/2016 | El-Kurdl et al. |
| 2003/0027332 | A1 | 2/2003 | Lafrance et al. |
| 2014/0329323 | A1 | 11/2014 | Nygaard et al. |
| 2014/0377213 | A1 | 12/2014 | Hong et al. |
| 2017/0081667 | A1 | 3/2017 | Chen et al. |
| 2017/0191082 | A1 | 7/2017 | Chen et al. |

OTHER PUBLICATIONS

Mo et al. (Int J Artif Organs, Aug. 2006;29(8):790-799).*

Zhao et al. (International Journal of Molecular Medicine, 2015 vol. 36:857-864).*

Estrada et al. (Cell Death and Disease, 2013 vol. 4:e691, pp. 1-13).*

Yamada et al., "Activation of STAT5 confers imatinib resistance on leukemic cells through the transcription of TERT and MDR1", Cellular Signalling, 2011, pp. 1119-1127, vol. 23.

Yamada et al., "JAK-STAT and JAK-PI3K-mTORC1 Pathways Regulate Telomerase Transcriptionally and Posttranslationally in ATL Cells", Mol Cancer Ther, 2012, pp. 1112-1121, vol. 11, No. 5.

Yamada et al., "The role of the JAK-STAT pathway and related signal cascades in telomerase activation during the development of hematologic malignancies", JAK-STAT, 2013, Article No. e25256, 10 pages, vol. 2, No. 4.

Yang et al., "The A2B adenosine receptor protects against inflammation and excessive vascular adhesion", The Journal of Clinical Investigation, 2006, pp. 1913-1923, vol. 116, No. 7.

Yang et al., "Bone morphogenic protein 2 induces Runx2 and osteopontin expression in human aortic valve interstitial cells: Role of Smad1 and extracellular signal-regulated kinase 1/2", The Journal of Thoracic and Cardiovascular Surgery, 2009, pp. 1008-1015, vol. 138.

Yang et al., "Increased polyploidy in aortic vascular smooth muscle cells during aging is marked by cellular senescence", Aging Cell, 2007, pp. 257-260, vol. 6.

Yehuda et al., "Differential decrease in soluble and DNA-bound telomerase in senescent human fibroblasts", Biogerontology, 2017, pp. 525-533, vol. 18.

Yin et al., "NF-kB Regulates Transcription of the Mouse Telomerase Catalytic Subunit", The Journal of Biological Chemistry, 2000, pp. 36671-36675, vol. 275, No. 47.

Yip et al., "Calcification by Valve Interstitial Cells Is Regulated by the Stiffness of the Extracellular Matrix", Arterioscler Thromb Vase Biol, 2009, pp. 936-942, vol. 29.

Yutzey et al., "Calcific Aortic Valve Disease—A Consensus Summary From the Alliance of Investigators on Calcific Aortic Valve Disease", Arterioscler Thromb Vase Biol, 2014, pp. 2387-2393, vol. 34.

Zhang et al., "Human Telomerase Reverse Transcriptase (hTERT) is a Novel Target of the Wnt/Beta-Catenin Pathway in Human Cancer", The Journal of Biological Chemistry, 2012, pp. 32494-32511, vol. 287, No. 39.

Aggarwal et al., "Sex Differences in Aortic Valve Calcification Measured by Multidetector Computed Tomography in Aortic Stenosis", Circ Cardiovasc Imaging, 2013, pp. 40-47, vol. 6.

Alves et al., "Calcifying vascular smooth muscle cells and osteoblasts: independent cell types exhibiting extracellular matrix and biomineralization-related mimicries", BMC Genomics, 2014, 14 pages, vol. 15, No. 965.

Aono et al., "Telomerase Inhibition by Everolimus Suppresses Smooth Muscle Cell Proliferation and Neointima Formation Through Epigenetic Gene Silencing", J Am Coll Cardiol Basic Trans Sci, 2016, pp. 49-60, vol. 1, No. 1-2.

Babu et al., "Lipopolysaccharide Stimulation of Human Aortic Valve Interstitial Cells Activates Inflammation and Osteogenesis", Ann Thorac Surg, 2008, pp. 71-76, vol. 86.

Badylak, "Regenerative Medicine Approach to Heart Valve Replacement", Circulation, 2005, pp. 2715-2716, vol. 111.

Balachandran et al., "Elevated cyclic stretch alters matrix remodeling in aortic valve cusps: implications for degenerative aortic valve disease", Am J Physiol Heart Circ Physiol, 2009, pp. H756-H764, vol. 296.

Birmingham et al., "A protocol for designing siRNAs with high functionality and specificity", Nature Protocols, 2007, pp. 2068-2078, vol. 2, No. 9.

Blevins et al., "Phenotypic Characterization of Isolated Valvular Interstitial Cell Subpopulations", The Journal of Heart Valve Disease, 2006, pp. 815-822, vol. 15.

Bosse et al., "Refining Molecular Pathways Leading to Calcific Aortic Valve Stenosis by Studying Gene Expression Profile of Normal and Calcified Stenotic Human Aortic Valves", Circ Cardiovasc Genet, 2009, pp. 489-498, vol. 2.

Bostrom et al., "Bone Morphogenetic Protein Expression in Human Atherosclerotic Lesions", J. Clin. Invest., 1993, pp. 1800-1809, vol. 91.

Chen et al., "Cell-Matrix Interactions in the Pathobiology of Calcific Aortic Valve Disease: Critical Roles for Matricellular, Matricrine, and Matrix Mechanics Cues", Circ Res, 2011, pp. 1510-1524, vol. 108.

Chiang et al., "Expression of Telomerase RNA Template, but not Telomerase Reverse Transcriptase, Is Limiting for Telomere Length Maintenance In Vivo", Molecular and Cellular Biology, 2004, pp. 7024-7031, vol. 24, No. 16.

Chien et al., "Novel indoloquinoline derivative, IQDMA, suppresses STAT5 phosphorylation and induces apoptosis in HL-60 cells", Chemico-Biological Interactions, 2008, pp. 40-47, vol. 176.

Choi et al., "TERT Promotes Epithelial Proliferation through Transcriptional Control of a Myc- and Wnt-Related Developmental Program", PLoS Genetics, 2008, pp. 124-138, vol. 4, No. 1.

Clark et al., "Clinical and economic outcomes after surgical aortic valve replacement in Medicare patients", Risk Management and Healthcare Policy, 2012, pp. 117-126, vol. 5.

Cooley et al., "TGF-Beta Signaling Mediates Endothelial-to-Mesenchymal Transition (EndMT) During Vein Graft Remodeling", Science Translational Medicine, 2014, Article No. 227ra34, pp. 1-12, vol. 6, No. 227.

Corey, "Chemical modification: the key to clinical application of RNA interference?", The Journal of Clinical Investigation, 2007, pp. 3615-3622, vol. 117, No. 12.

(56) References Cited

OTHER PUBLICATIONS

Dieudonne et al., "Promotion of Osteoblast Differentiation in Mesenchymal Cells Through Cbl-Mediated Control of STAT5 Activity", Stem Cells, 2013, pp. 1340-1349, vol. 31.
Endorf et al., "Telomerase Reverse Transcriptase Deficiency Prevents Neointima Formation Through Chromatin Silencing of E2F1 Target Genes", Arterioscler Thromb Vasc Biol, 2017, pp. 301-311, vol. 37.
Fang et al., "Loss of Beta-Catenin Promotes Chondrogenic Differentiation of Aortic Valve Interstitial Cells", Arterioscler Thromb Vasc Biol, 2014, pp. 2601-2608, vol. 34.
Findeisen et al., "Telomerase Deficiency in Bone Marrow-Derived Cells Attenuates Angiotensin II-Induced Abdominal Aortic Aneurysm Formation", Arterioscler Thromb Vasc Biol, 2011, pp. 253-260, vol. 31.
Flores et al., "Effects of Telomerase and Telomere Length on Epidermal Stem Cell Behavior", Science, 2005, pp. 1253-1256, vol. 309.
Fredriksson et al., "Protein detection using proximity-dependent DNA ligation assays", Nature Biotechnology, 2002, pp. 473-477, vol. 20.
Friedbichler et al., "Stat5a serine 725 and 779 phosphorylation is a prerequisite for hematopoietic transformation", Blood, 2010, pp. 1548-1558, vol. 116, No. 9.
Friedrich et al., "Telomere length in different tissues of elderly patients", Mechanisms of Ageing and Development, 2000, pp. 89-99, vol. 119.
Galas et al., "Aortic valve calcification in 499 consecutive patients referred for computed tomography", Arch Med Sci, 2015, pp. 952-957, vol. 11, No. 5.
Gizard et al., "Telomerase Activation in Atherosclerosis and Induction of Telomerase Reverse Transcriptase Expression by Inflammatory Stimuli in Macrophages", Arterioscler Thromb Vasc Biol, 2011, pp. 245-252, vol. 31.
Gould et al., "Cyclic strain anisotropy regulates valvular interstitial cell phenotype and tissue remodeling in three-dimensional culture", Acta Biomaterialia, 2012, pp. 1710-1719, vol. 8.
Gu et al., "Role of Wnt/Beta-catenin Signaling Pathway in the Mechanism of Calcification of Aortic Valve", J Huazhong Univ Sci Technol (Med Sci), 2014, pp. 33-36, vol. 34, No. 1.
Guauque-Olarte et al., "Calcium Signaling Pathway Genes RUNX2 and CACNA1C Are Associated With Calcific Aortic Valve Disease", Circ Cardiovasc Genet, 2015, pp. 812-822, vol. 8.
Gundry et al., "Highly Efficient Genome Editing of Murine and Human Hematopoietic Progenitor Cells by CRISPR/Cas9", Cell Reports, 2016, pp. 1453-1461, vol. 17.
Hao et al., "Short Telomeres, even in the Presence of Telomerase, Limit Tissue Renewal Capacity", Cell, 2005, pp. 1121-1131, vol. 123.
Heidenreich et al., "Forecasting the Impact of Heart Failure in the United States: A Policy Statement From the American Heart Association", Circ Heart Fail, 2013, pp. 606-619, vol. 6.
Hoemann et al., "In vitro osteogenesis assays: Influence of the primary cell source on alkaline phosphatase activity and mineralization", Pathologie Biologie, 2009, pp. 318-323, vol. 57.
Hong et al., "Tailoring the degradation kinetics of polyfester carbonate urethane)urea thermoplastic elastomers for tissue engineering scaffolds", Biomaterials, 2010, pp. 4249-4258, vol. 31.
Hortells et al., "Abstract 480: A Novel Role for Telomerase in Calcific Aortic Valve Disease", Circulation Research, 2019, Abstract A480, Supplement 125.
Hortells et al., "The role of telomerase and senescence in aortic valve calcification", Poster Abstract, presented May 2017.
Hutcheson et al., "Genesis and growth of extracellular-vesicle-derived microcalcification in atherosclerotic plaques", Nature Materials, 2016, pp. 335-345, vol. 15.
Huveneers et al., "Mechanosensitive systems at the cadherin-F-actin interface", Journal of Cell Science, 2013, pp. 403-413, vol. 126.
Jana et al., "Cells for tissue engineering of cardiac valves", Journal of Tissue Engineering and Regenerative Medicine, 2016, pp. 804-824, vol. 10.
Jian et al., "Progression of Aortic Valve Stenosis: TGF-Beta1 is Present in Calcified Aortic Valve Cusps and Promotes Aortic Valve Interstitial Cell Calcification Via Apoptosis", Ann Thorac Surg, 2003, pp. 457-466, vol. 75.
Jiang et al., "CRISPR-Cas9 Structures and Mechanisms", Annu. Rev. Biophys., 2017, pp. 505-529, vol. 46.
Jin et al., "Increased activity of TNAP compensates for reduced adenosine production and promotes ectopic calcification in the genetic disease ACDC", Sci Signal, 2017, Article No. ra121, vol. 9, No. 458.
Joung et al., "MSM Enhances GH Signaling via the Jak2/STAT5b Pathway in Osteoblast-Like Cells and Osteoblast Differentiation through the Activation of STAT5b in MSCs", PLoS ONE, 2012, Article No. e47477, vol. 7, No. 10.
Joung et al., "TALENs: a widely applicable technology for targeted genome editing", Nature Reviews: Molecular Cell Biology, 2013, pp. 49-55, vol. 14.
Kanisicak et al., "Genetic lineage tracing defines myofibroblast origin and function in the injured heart", Nature Communications, 2016, Article No. 7:12260, pp. 1-14, DOI: 10.1038/ncomms12260.
Kim et al., "Specific Association of Human Telomerase Activity with Immortal Cells and Cancer", Science, 1994, pp. 2011-2015, vol. 266.
Komori et al., "Targeted Disruption of Cbfa1 Results in a Complete Lack of Bone Formation owing to Maturational Arrest of Osteoblasts", Cell, 1997, pp. 755-764, vol. 89.
Konnikova et al., "Signal Transducer and Activator of Transcription 3 (STAT3) Regulates Human Telomerase Reverse Transcriptase (hTERT) Expression in Human Cancer and Primary Cells", Cancer Res, 2005, pp. 6516-6520, vol. 65, No. 15.
Kotterman et al., "Engineering adeno-associated viruses for clinical gene therapy", Nature Reviews: Genetics, 2014, pp. 445-451, vol. 15.
Kovacic et al., "Stat3-dependent acute Rantes production in vascular smooth muscle cells modulates inflammation following arterial injury in mice", The Journal of Clinical Investigation, 2010, pp. 303-314, vol. 120.
Kurz et al., "Degenerative Aortic Valve Stenosis, but not Coronary Disease, Is Associated With Shorter Telomere Length in the Elderly", Arterioscler Thromb Vasc Biol, 2006, pp. e114-e117, vol. 26.
Kuscu et al., "CRISPR-STOP: gene silencing through base-editing-induced nonsense mutations", Nature Methods, 2017, pp. 710-712, vol. 14, No. 7.
Lanzer et al., "Medial vascular calcification revisited: review and perspectives", European Heart Journal, 2014, pp. 1515-1525, vol. 35.
Latif et al., "Characterization of Structural and Signaling Molecules by Human Valve Interstitial Cells and Comparison to Human Mesenchymal Stem Cells", The Journal of Heart Valve Disease, 2007, pp. 56-66, vol. 16.
Lee et al., "Lasagna: A novel algorithm for transcription factor binding site alignment", BMC Bioinformatics, 2013, 13 pages, vol. 14, No. 108.
Leopold, "Cellular Mechanisms of Aortic Valve Calcification", Circ Cardiovasc Interv, 2012, pp. 605-614, vol. 5.
Levy et al., "STATS: Transcriptional Control and Biological Impact", Nature Reviews: Molecular Cell Biology, 2002, pp. 651-662, vol. 3.
Li et al., "Non-canonical NF-kB signalling and ETS1/2 cooperatively drive C250T mutant TERT promoter activation", Nature Cell Biology, 2015, pp. 1327-1338, vol. 17, No. 10.
Lin et al., "Runx2 Expression in Smooth Muscle Cells Is Required for Arterial Medial Calcification in Mice", Am J Pathol, 2015, pp. 1958-1969, vol. 185, No. 7.
Lindsley et al., "Identification and characterization of a novel Schwann and outflow tract endocardial cushion lineage-restricted periostin enhancer", Developmental Biology, 2007, pp. 340-355, vol. 307.
Liu et al., "Characterization of cell motility in single heart valve interstitial cells in vitro", Histol Histopathol, 2007, pp. 373-882, vol. 22.

(56) References Cited

OTHER PUBLICATIONS

Liu et al., "The Emerging Role of Valve Interstitial Cell Phenotypes in Regulating Heart Valve Pathobiology", The American Journal of Pathology, 2007, pp. 1407-1418, vol. 171, No. 5.
Luo et al., "Spontaneous calcification of arteries and cartilage in mice lacking matrix GLA protein", Nature, 1997, pp. 78-81, vol. 386.
Masutomi et al., "The telomerase reverse transcriptase regulates chromatin state and DNA damage responses", PNAS, 2005, pp. 8222-8227, vol. 102, No. 23.
Matthews et al., "Vascular Smooth Muscle Cells Undergo Telomere-Based Senescence in Human Atherosclerosis—Effects of Telomerase and Oxidative Stress", Circ Res, 2006, pp. 156-164, vol. 99.
Nishimura et al., "2014 AHA/ACC Guideline for the Management of Patients With Valvular Heart Disease: Executive Summary—A report of the American College of Cardiology/American Heart Association Task Force on Practice Guidelines", Circulation, 2014, pp. 2440-2492, vol. 129.
Oka et al., "Genetic Manipulation of Periostin Expression Reveals a Role in Cardiac Hypertrophy and Ventricular Remodeling", Circ Res, 2007, pp. 313-321, vol. 101.
Okutani et al., "Src directly tyrosine-phosphorylates STAT5 on its activation site and is involved in erythropoietin-induced signaling pathway", Oncogene, 2001, pp. 6643-6650, vol. 20.
Orita et al., "Role of Osteoprotegerin in Arterial Calcification—Development of New Animal Model", Arterioscler Thromb Vase Biol, 2007, pp. 2058-2064, vol. 27.
O'Rourke et al., "Calcification of Vascular Smooth Muscle Cells and Imaging of Aortic Calcification and Inflammation", J. Vis. Exp., 2016, Article No. e54017, pp. 1-13, vol. 111.
Park et al., "Telomerase modulates Wnt signalling by association with target gene chromatin", Nature, 2009, pp. 66-72, vol. 460.
Pascolo et al., "Mechanism of Human Telomerase Inhibition by BIBR1532, a Synthetic, Non-nucleosidic Drug Candidate", The Journal of Biological Chemistry, 2002, pp. 15566-15572, vol. 277, No. 18.
Ponte et al., "Human Actin Genes Are Single Copy for alpha-Skeletal and alpha-Cardiac Actin but Multicopy for beta- and gamma-Cytoskeletal Genes: 3' Untranslated Regions are Isotype Specific but are Conserved in Evolution", Molecular and Cellular Biology, 1983, pp. 1783-1791, vol. 3, No. 10.
Prakash et al., "A Roadmap to Investigate the Genetic Basis of Bicuspid Aortic Valve and its Complications", J Am Coll Cardiol, 2014, pp. 832-839, vol. 64.
Qing et al., "Differential Regulation of Telomerase Reverse Transcriptase Promoter Activation and Protein Degradation by Histone Deacetylase Inhibition", J. Cell. Physiol., 2016, pp. 1276-1282, vol. 231.
Raposio et al., "Adipose-derived stem cells: Comparison between two methods of isolation for clinical applications", Annals of Medicine and Surgery, 2017, pp. 87-91, vol. 20.
Rodriguez et al., "MEF2B-Nox1 Signaling is Critical for Stretch-Induced Phenotypic Modulation of Vascular Smooth Muscle Cells", Arterioscler Thromb Vase Biol, 2015, pp. 430-438, vol. 35.
Ruiz et al., "Zooming in on the genesis of atherosclerotic plaque microcalcifications", J Physiol, 2016, pp. 2915-2927, vol. 594, No. 11.
Rutkovskiy et al., "Valve Interstitial Cells: The Key to Understanding the Pathophysiology of Heart Valve Calcification", Journal of the American Heart Association, 2017, Article No. e006339, pp. 1-23, vol. 6.
Sadelain et al., "Safe harbours for the integration of new DNA in the human genome", Nature Reviews—Cancer, 2012, pp. 51-58, vol. 12.
Sarin et al., "Conditional telomerase induction causes proliferation of hair follicle stem cells", Nature, 2005, pp. 1048-1052, vol. 436.
Shi et al., "Bone formation by human postnatal bone marrow stromal stem cells is enhanced by telomerase expression", Nature Biotechnology, 2002, pp. 587-591, vol. 20.
Simonsen et al., "Telomerase expression extends the proliferative life-span and maintains the osteogenic potential of human bone marrow stromal cells", Nature Biotechnology, 2002, pp. 592-596, vol. 20.
Slagboom et al., "Genetic Determination of Telomere Size in Humans: A Twin Study of Three Age Groups", Am. J. Hum. Genet., 1994, pp. 876-882, vol. 55.
Smith et al., "Telomerase modulates expression of growth-controlling genes and enhances cell proliferation", Nature Cell Biology, 2003, pp. 474-479, vol. 5.
Song et al., "An epigenetic regulatory loop controls pro-osteogenic activation by TGF-Beta1 or bone morphogenetic protein 2 in human aortic valve interstitial cells", J. Biol. Chem., 2017, pp. 8657-8666, vol. 292, No. 21.
Stewart et al., "Telomerase contributes to tumorigenesis by a telomere length-independent mechanism", PNAS, 2002, pp. 12606-12611, vol. 99, No. 20.
St. Hilaire et al., "NT5E Mutations and Arterial Calcifications", The New England Journal of Medicine, 2011, pp. 432-442, vol. 364.
Sutherland et al., "From Stem Cells to Viable Autologous Semilunar Heart Valve", Circulation, 2005, pp. 2783-2791, vol. 111.
Taylor et al., "The cardiac valve interstitial cell", The International Journal of Biochemistry & Cell Biology, 2003, pp. 113-118, vol. 35.
Vande Geest et al., "An analysis of the complete strain field within Flexercell membranes", Journal of Biomechanics, 2004, pp. 1923-1928, vol. 37.
Vedepo et al., "Recellularization of decellularized heart valves: Progress toward the tissue-engineered heart valve", Journal of Tissue Engineering, 2017, pp. 1-21, vol. 8.
Venardos et al., "Matrix Gia protein regulates calcification of the aortic valve", Journal of Surgical Research, 2015, pp. 1-6, vol. 199.
Vogel et al., "U.S. Researchers Recognized for Work on Telomeres", Science, 2009, pp. 212-213, vol. 326.
Walker et al., "Valvular Myofibroblast Activation by Transforming Growth Factor-beta: Implications for Pathological Extracellular Matrix Remodeling in Heart Valve Disease", Circ Res., 2004, pp. 253-260, vol. 95.
Wang et al., "Characterization of Cell Subpopulations Expressing Progenitor Cell Markers in Porcine Cardiac Valves", PLoS ONE, 2013, Article No. e69667, vol. 8, No. 7.
Watts et al., "Silencing disease genes in the laboratory and the clinic", Journal of Pathology, 2012, pp. 365-379, vol. 226.
Wright, "The microscopical appearances of human peripheral arteries during growth and aging", J. Clin. Path., 1963, pp. 499-522, vol. 16.
Xue et al., "Shape-Specific Nanoceria Mitigate Oxidative Stress-Induced Calcification in Primary Human Valvular Interstitial Cell Culture", Cellular and Molecular Bioengineering, 2017, pp. 483-500, vol. 10, No. 5.

* cited by examiner

>NM_001193376.1 Homo sapiens telomerase reverse transcriptase (TERT), transcript variant 2, mRNA (SEQ ID NO: 1)

CAGGCAGCGCTGCGTCCTGCTGCGCACGTGGGAAGCCCTGGCCCCGGCCACCCCCGCGATGCCGCGCGCT
CCCCGCTGCCGAGCCGTGCGCTCCCTGCTGCGCAGCCACTACCGCGAGGTGCTGCCGCTGGCCACGTTCG
TGCGGCGCCTGGGGCCCCAGGGCTGGCGGCTGGTGCAGCGCGGGGACCCGGCGGCTTTCCGCGCGCTGGT
GGCCCAGTGCCTGGTGTGCGTGCCCTGGGACGCACGGCCGCCCCCCGCCGCCCCCTCCTTCCGCCAGGTG
TCCTGCCTGAAGGAGCTGGTGGCCCGAGTGCTGCAGAGGCTGTGCGAGCGCGGCGCGAAGAACGTGCTGG
CCTTCGGCTTCGCGCTGCTGGACGGGGCCCGCGGGGGCCCCCCCGAGGCCTTCACCACCAGCGTGCGCAG
CTACCTGCCCAACACGGTGACCGACGCACTGCGGGGGAGCGGGGCGTGGGGGCTGCTGCTGCGCCGCGTG
GGCGACGACGTGCTGGTTCACCTGCTGGCACGCTGCGCGCTCTTTGTGCTGGTGGCTCCCAGCTGCGCCT
ACCAGGTGTGCGGGCCGCCGCTGTACCAGCTCGGCGCTGCCACTCAGGCCCGGCCCCCGCCACACGCTAG
TGGACCCCGAAGGCGTCTGGGATGCGAACGGGCCTGGAACCATAGCGTCAGGGAGGCCGGGGTCCCCCTG
GGCCTGCCAGCCCCGGGTGCGAGGAGGCGCGGGGGCAGTGCCAGCCGAAGTCTGCCGTTGCCCAAGAGGC
CCAGGCGTGGCGCTGCCCCTGAGCCGGAGCGGACGCCCGTTGGGCAGGGGTCCTGGGCCCACCCGGGCAG
GACGCGTGGACCGAGTGACCGTGGTTTCTGTGTGGTGTCACCTGCCAGACCCGCCGAAGAAGCCACCTCT
TTGGAGGGTGCGCTCTCTGGCACGCGCCACTCCCACCCATCCGTGGGCCGCCAGCACCACGCGGGCCCCC
CATCCACATCGCGGCCACCACGTCCCTGGGACACGCCTTGTCCCCCGGTGTACGCCGAGACCAAGCACTT
CCTCTACTCCTCAGGCGACAAGGAGCAGCTGCGGCCCTCCTTCCTACTCAGCTCTCTGAGGCCCAGCCTG
ACTGGCGCTCGGAGGCTCGTGGAGACCATCTTTCTGGGTTCCAGGCCCTGGATGCCAGGGACTCCCCGCA
GGTTGCCCCGCCTGCCCCAGCGCTACTGGCAAATGCGGCCCCTGTTTCTGGAGCTGCTTGGGAACCACGC
GCAGTGCCCCTACGGGGTGCTCCTCAAGACGCACTGCCCGCTGCGAGCTGCGGTCACCCCAGCAGCCGGT
GTCTGTGCCCGGGAGAAGCCCCAGGGCTCTGTGGCGGCCCCCGAGGAGGAGGACACAGACCCCCGTCGCC
TGGTGCAGCTGCTCCGCCAGCACAGCAGCCCCTGGCAGGTGTACGGCTTCGTGCGGGCCTGCCTGCGCCG
GCTGGTGCCCCCAGGCCTCTGGGGCTCCAGGCACAACGAACGCCGCTTCCTCAGGAACACCAAGAAGTTC
ATCTCCCTGGGGAAGCATGCCAAGCTCTCGCTGCAGGAGCTGACGTGGAAGATGAGCGTGCGGGACTGCG
CTTGGCTGCGCAGGAGCCCAGGGGTTGGCTGTGTTCCGGCCGCAGAGCACCGTCTGCGTGAGGAGATCCT
GGCCAAGTTCCTGCACTGGCTGATGAGTGTGTACGTCGTCGAGCTGCTCAGGTCTTTCTTTTATGTCACG
GAGACCACGTTTCAAAAGAACAGGCTCTTTTTCTACCGGAAGAGTGTCTGGAGCAAGTTGCAAAGCATTG
GAATCAGACAGCACTTGAAGAGGGTGCAGCTGCGGGAGCTGTCGGAAGCAGAGGTCAGGCAGCATCGGGA
AGCCAGGCCCGCCCTGCTGACGTCCAGACTCCGCTTCATCCCCAAGCCTGACGGGCTGCGGCCGATTGTG
AACATGGACTACGTCGTGGGAGCCAGAACGTTCCGCAGAGAAAAGAGGGCCGAGCGTCTCACCTCGAGGG
TGAAGGCACTGTTCAGCGTGCTCAACTACGAGCGGGCGCGGCGCCCCGGCCTCCTGGGCGCCTCTGTGCT
GGGCCTGGACGATATCCACAGGGCCTGGCGCACCTTCGTGCTGCGTGTGCGGGCCCAGGACCCGCCGCCT
GAGCTGTACTTTGTCAAGGTGGATGTGACGGGCGCGTACGACACCATCCCCCAGGACAGGCTCACGGAGG
TCATCGCCAGCATCATCAAACCCCAGAACACGTACTGCGTGCGTCGGTATGCCGTGGTCCAGAAGGCCGC
CCATGGGCACGTCCGCAAGGCCTTCAAGAGCCACGTCTCTACCTTGACAGACCTCCAGCCGTACATGCGA
CAGTTCGTGGCTCACCTGCAGGAGACCAGCCCGCTGAGGGATGCCGTCGTCATCGAGCAGAGCTCCTCCC
TGAATGAGGCCAGCAGTGGCCTCTTCGACGTCTTCCTACGCTTCATGTGCCACCACGCCGTGCGCATCAG
GGGCAAGTCCTACGTCCAGTGCCAGGGGATCCCGCAGGGCTCCATCCTCTCCACGCTGCTCTGCAGCCTG
TGCTACGGCGACATGGAGAACAAGCTGTTTGCGGGGATTCGGCGGGACGGGCTGCTCCTGCGTTTGGTGG
ATGATTTCTTGTTGGTGACACCTCACCTCACCCACGCGAAAACCTTCCTCAGCTATGCCCGGACCTCCAT
CAGAGCCAGTCTCACCTTCAACCGCGGCTTCAAGGCTGGGAGGAACATGCGTCGCAAACTCTTTGGGGTC
TTGCGGCTGAAGTGTCACAGCCTGTTTCTGGATTTGCAGGTGAACAGCCTCCAGACGGTGTGCACCAACA
TCTACAAGATCCTCCTGCTGCAGGCGTACAGGTTTCACGCATGTGTGCTGCAGCTCCCATTTCATCAGCA
AGTTTGGAAGAACCCCACATTTTTCCTGCGCGTCATCTCTGACACGGCCTCCCTCTGCTACTCCATCCTG
AAAGCCAAGAACGCAGGGATGTCGCTGGGGGCCAAGGGCGCCGCCGGCCCTCTGCCCTCCGAGGCCGTGC
AGTGGCTGTGCCACCAAGCATTCCTGCTCAAGCTGACTCGACACCGTGTCACCTACGTGCCACTCCTGGG
GTCACTCAGGACAGCCCAGACGCAGCTGAGTCGGAAGCTCCCGGGGACGACGCTGACTGCCCTGGAGGCC
GCAGCCAACCCGGCACTGCCCTCAGACTTCAAGACCATCCTGGACTGATGGCCACCCGCCCACAGCCAGG

FIG. 1-1

CCGAGAGCAGACACCAGCAGCCCTGTCACGCCGGGCTCTACGTCCCAGGGAGGGAGGGGCGGCCCACACC
CAGGCCCGCACCGCTGGGAGTCTGAGGCCTGAGTGAGTGTTTGGCCGAGGCCTGCATGTCCGGCTGAAGG
CTGAGTGTCCGGCTGAGGCCTGAGCGAGTGTCCAGCCAAGGGCTGAGTGTCCAGCACACCTGCCGTCTTC
ACTTCCCCACAGGCTGGCGCTCGGCTCCACCCCAGGGCCAGCTTTTCCTCACCAGGAGCCCGGCTTCCAC
TCCCCACATAGGAATAGTCCATCCCCAGATTCGCCATTGTTCACCCCTCGCCCTGCCCTCCTTTGCCTTC
CACCCCCACCATCCAGGTGGAGACCCTGAGAAGGACCCTGGGAGCTCTGGGAATTTGGAGTGACCAAAGG
TGTGCCCTGTACACAGGCGAGGACCCTGCACCTGGATGGGGGTCCCTGTGGGTCAAATTGGGGGGAGGTG
CTGTGGGAGTAAAATACTGAATATATGAGTTTTTCAGTTTTGAAAAAAA

>NM_198253.2 Homo sapiens telomerase reverse transcriptase (TERT), transcript variant 1, mRNA (SEQ ID NO: 2)

CAGGCAGCGCTGCGTCCTGCTGCGCACGTGGGAAGCCCTGGCCCCGGCCACCCCCGCGATGCCGCGCGCT
CCCCGCTGCCGAGCCGTGCGCTCCCTGCTGCGCAGCCACTACCGCGAGGTGCTGCCGCTGGCCACGTTCG
TGCGGCGCCTGGGGCCCCAGGGCTGGCGGCTGGTGCAGCGCGGGGACCCGGCGGCTTTCCGCGCGCTGGT
GGCCCAGTGCCTGGTGTGCGTGCCCTGGGACGCACGGCCGCCCCCCGCCGCCCCCTCCTTCCGCCAGGTG
TCCTGCCTGAAGGAGCTGGTGGCCCGAGTGCTGCAGAGGCTGTGCGAGCGCGGCGCGAAGAACGTGCTGG
CCTTCGGCTTCGCGCTGCTGGACGGGGCCCGCGGGGGCCCCCCCGAGGCCTTCACCACCAGCGTGCGCAG
CTACCTGCCCAACACGGTGACCGACGCACTGCGGGGGAGCGGGGCGTGGGGGCTGCTGCTGCGCCGCGTG
GGCGACGACGTGCTGGTTCACCTGCTGGCACGCTGCGCGCTCTTTGTGCTGGTGGCTCCCAGCTGCGCCT
ACCAGGTGTGCGGGCCGCCGCTGTACCAGCTCGGCGCTGCCACTCAGGCCCGGCCCCCGCCACACGCTAG
TGGACCCCGAAGGCGTCTGGGATGCGAACGGGCCTGGAACCATAGCGTCAGGGAGGCCGGGGTCCCCCTG
GGCCTGCCAGCCCCGGGTGCGAGGAGGCGCGGGGGCAGTGCCAGCCGAAGTCTGCCGTTGCCCAAGAGGC
CCAGGCGTGGCGCTGCCCCTGAGCCGGAGCGGACGCCCGTTGGGCAGGGGTCCTGGGCCCACCCGGGCAG
GACGCGTGGACCGAGTGACCGTGGTTTCTGTGTGGTGTCACCTGCCAGACCCGCCGAAGAAGCCACCTCT
TTGGAGGGTGCGCTCTCTGGCACGCGCCACTCCCACCCATCCGTGGGCCGCCAGCACCACGCGGGCCCCC
CATCCACATCGCGGCCACCACGTCCCTGGGACACGCCTTGTCCCCCGGTGTACGCCGAGACCAAGCACTT
CCTCTACTCCTCAGGCGACAAGGAGCAGCTGCGGCCCTCCTTCCTACTCAGCTCTCTGAGGCCCAGCCTG
ACTGGCGCTCGGAGGCTCGTGGAGACCATCTTTCTGGGTTCCAGGCCCTGGATGCCAGGGACTCCCCGCA
GGTTGCCCCGCCTGCCCCAGCGCTACTGGCAAATGCGGCCCCTGTTTCTGGAGCTGCTTGGGAACCACGC
GCAGTGCCCCTACGGGGTGCTCCTCAAGACGCACTGCCCGCTGCGAGCTGCGGTCACCCCAGCAGCCGGT
GTCTGTGCCCGGGAGAAGCCCCAGGGCTCTGTGGCGGCCCCCGAGGAGGAGGACACAGACCCCCGTCGCC
TGGTGCAGCTGCTCCGCCAGCACAGCAGCCCCTGGCAGGTGTACGGCTTCGTGCGGGCCTGCCTGCGCCG
GCTGGTGCCCCCAGGCCTCTGGGGCTCCAGGCACAACGAACGCCGCTTCCTCAGGAACACCAAGAAGTTC
ATCTCCCTGGGGAAGCATGCCAAGCTCTCGCTGCAGGAGCTGACGTGGAAGATGAGCGTGCGGGACTGCG
CTTGGCTGCGCAGGAGCCCAGGGGTTGGCTGTGTTCCGGCCGCAGAGCACCGTCTGCGTGAGGAGATCCT
GGCCAAGTTCCTGCACTGGCTGATGAGTGTGTACGTCGTCGAGCTGCTCAGGTCTTTCTTTTATGTCACG
GAGACCACGTTTCAAAAGAACAGGCTCTTTTTCTACCGGAAGAGTGTCTGGAGCAAGTTGCAAAGCATTG
GAATCAGACAGCACTTGAAGAGGGTGCAGCTGCGGGAGCTGTCGGAAGCAGAGGTCAGGCAGCATCGGGA
AGCCAGGCCCGCCCTGCTGACGTCCAGACTCCGCTTCATCCCCAAGCCTGACGGGCTGCGGCCGATTGTG
AACATGGACTACGTCGTGGGAGCCAGAACGTTCCGCAGAGAAAAGAGGGCCGAGCGTCTCACCTCGAGGG
TGAAGGCACTGTTCAGCGTGCTCAACTACGAGCGGGCGCGGCGCCCCGGCCTCCTGGGCGCCTCTGTGCT
GGGCCTGGACGATATCCACAGGGCCTGGCGCACCTTCGTGCTGCGTGTGCGGGCCCAGGACCCGCCGCCT
GAGCTGTACTTTGTCAAGGTGGATGTGACGGGCGCGTACGACACCATCCCCCAGGACAGGCTCACGGAGG
TCATCGCCAGCATCATCAAACCCCAGAACACGTACTGCGTGCGTCGGTATGCCGTGGTCCAGAAGGCCGC
CCATGGGCACGTCCGCAAGGCCTTCAAGAGCCACGTCTCTACCTTGACAGACCTCCAGCCGTACATGCGA
CAGTTCGTGGCTCACCTGCAGGAGACCAGCCCGCTGAGGGATGCCGTCGTCATCGAGCAGAGCTCCTCCC
TGAATGAGGCCAGCAGTGGCCTCTTCGACGTCTTCCTACGCTTCATGTGCCACCACGCCGTGCGCATCAG
GGGCAAGTCCTACGTCCAGTGCCAGGGGATCCCGCAGGGCTCCATCCTCTCCACGCTGCTCTGCAGCCTG

FIG. 1-2

TGCTACGGCGACATGGAGAACAAGCTGTTTGCGGGGATTCGGCGGGACGGGCTGCTCCTGCGTTTGGTGG
ATGATTTCTTGTTGGTGACACCTCACCTCACCCACGCGAAAACCTTCCTCAGGACCCTGGTCCGAGGTGT
CCCTGAGTATGGCTGCGTGGTGAACTTGCGGAAGACAGTGGTGAACTTCCCTGTAGAAGACGAGGCCCTG
GGTGGCACGGCTTTTGTTCAGATGCCGGCCCACGGCCTATTCCCCTGGTGCGGCCTGCTGCTGGATACCC
GGACCCTGGAGGTGCAGAGCGACTACTCCAGCTATGCCCGGACCTCCATCAGAGCCAGTCTCACCTTCAA
CCGCGGCTTCAAGGCTGGGAGGAACATGCGTCGCAAACTCTTTGGGGTCTTGCGGCTGAAGTGTCACAGC
CTGTTTCTGGATTTGCAGGTGAACAGCCTCCAGACGGTGTGCACCAACATCTACAAGATCCTCCTGCTGC
AGGCGTACAGGTTTCACGCATGTGTGCTGCAGCTCCCATTTCATCAGCAAGTTTGGAAGAACCCCACATT
TTTCCTGCGCGTCATCTCTGACACGGCCTCCCTCTGCTACTCCATCCTGAAAGCCAAGAACGCAGGGATG
TCGCTGGGGGCCAAGGGCGCCGCCGGCCCTCTGCCCTCCGAGGCCGTGCAGTGGCTGTGCCACCAAGCAT
TCCTGCTCAAGCTGACTCGACACCGTGTCACCTACGTGCCACTCCTGGGGTCACTCAGGACAGCCCAGAC
GCAGCTGAGTCGGAAGCTCCCGGGGACGACGCTGACTGCCCTGGAGGCCGCAGCCAACCCGGCACTGCCC
TCAGACTTCAAGACCATCCTGGACTGATGGCCACCCGCCCACAGCCAGGCCGAGAGCAGACACCAGCAGC
CCTGTCACGCCGGGCTCTACGTCCCAGGGAGGGAGGGGCGGCCCACACCCAGGCCCGCACCGCTGGGAGT
CTGAGGCCTGAGTGAGTGTTTGGCCGAGGCCTGCATGTCCGGCTGAAGGCTGAGTGTCCGGCTGAGGCCT
GAGCGAGTGTCCAGCCAAGGGCTGAGTGTCCAGCACACCTGCCGTCTTCACTTCCCCACAGGCTGGCGCT
CGGCTCCACCCCAGGGCCAGCTTTTCCTCACCAGGAGCCCGGCTTCCACTCCCCACATAGGAATAGTCCA
TCCCCAGATTCGCCATTGTTCACCCCTCGCCCTGCCCTCCTTTGCCTTCCACCCCCACCATCCAGGTGGA
GACCCTGAGAAGGACCCTGGGAGCTCTGGGAATTTGGAGTGACCAAAGGTGTGCCCTGTACACAGGCGAG
GACCCTGCACCTGGATGGGGGTCCCTGTGGGTCAAATTGGGGGGAGGTGCTGTGGGAGTAAAATACTGAA
TATATGAGTTTTTCAGTTTTGAAAAAAA

>NP_937983.2 telomerase reverse transcriptase isoform 1 [Homo sapiens] (SEQ ID NO: 3)
MPRAPRCRAVRSLLRSHYREVLPLATFVRRLGPQGWRLVQRGDPAAFRALVAQCLVCVPWDARPPPAAPS
FRQVSCLKELVARVLQRLCERGAKNVLAFGFALLDGARGGPPEAFTTSVRSYLPNTVTDALRGSGAWGLL
LRRVGDDVLVHLLARCALFVLVAPSCAYQVCGPPLYQLGAATQARPPPHASGPRRRLGCERAWNHSVREA
GVPLGLPAPGARRRGGSASRSLPLPKRPRRGAAPEPERTPVGQGSWAHPGRTRGPSDRGFCVVSPARPAE
EATSLEGALSGTRHSHPSVGRQHHAGPPSTSRPPRPWDTPCPPVYAETKHFLYSSGDKEQLRPSFLLSSL
RPSLTGARRLVETIFLGSRPWMPGTPRRLPRLPQRYWQMRPLFLELLGNHAQCPYGVLLKTHCPLRAAVT
PAAGVCAREKPQGSVAAPEEEDTDPRRLVQLLRQHSSPWQVYGFVRACLRRLVPPGLWGSRHNERRFLRN
TKKFISLGKHAKLSLQELTWKMSVRDCAWLRRSPGVGCVPAAEHRLREEILAKFLHWLMSVYVVELLRSF
FYVTETTFQKNRLFFYRKSVWSKLQSIGIRQHLKRVQLRELSEAEVRQHREARPALLTSRLRFIPKPDGL
RPIVNMDYVVGARTFRREKRAERLTSRVKALFSVLNYERARRPGLLGASVLGLDDIHRAWRTFVLRVRAQ
DPPPELYFVKVDVTGAYDTIPQDRLTEVIASIIKPQNTYCVRRYAVVQKAAHGHVRKAFKSHVSTLTDLQ
PYMRQFVAHLQETSPLRDAVVIEQSSSLNEASSGLFDVFLRFMCHHAVRIRGKSYVQCQGIPQGSILSTL
LCSLCYGDMENKLFAGIRRDGLLLRLVDDFLLVTPHLTHAKTFLRTLVRGVPEYGCVVNLRKTVVNFPVE
DEALGGTAFVQMPAHGLFPWCGLLLDTRTLEVQSDYSSYARTSIRASLTFNRGFKAGRNMRRKLFGVLRL
KCHSLFLDLQVNSLQTVCTNIYKILLLQAYRFHACVLQLPFHQQVWKNPTFFLRVISDTASLCYSILKAK
NAGMSLGAKGAAGPLPSEAVQWLCHQAFLLKLTRHRVTYVPLLGSLRTAQTQLSRKLPGTTLTALEAAAN
PALPSDFKTILD

FIG. 1-3

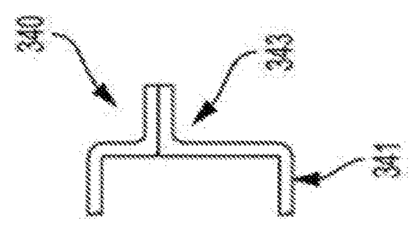
FIG. 3C
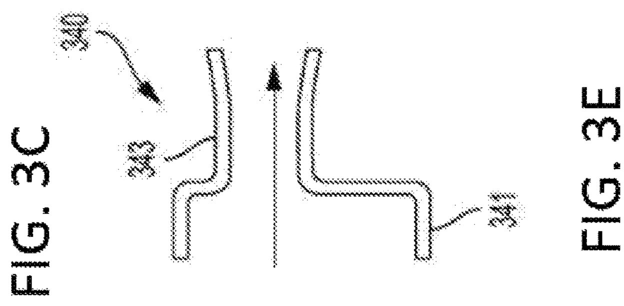
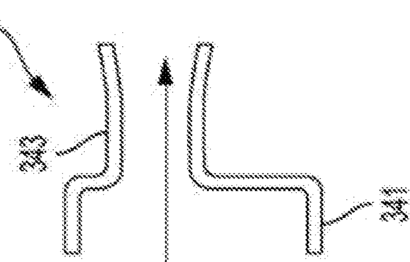
FIG. 3E
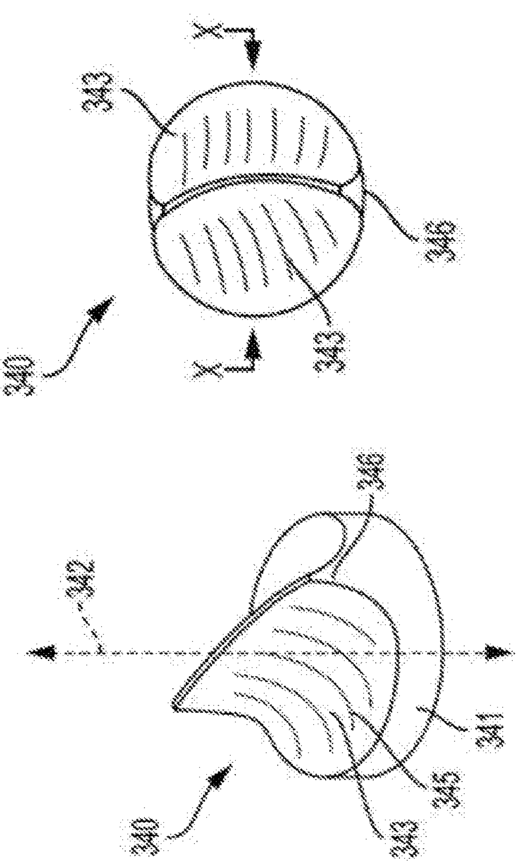
FIG. 3B
FIG. 3A
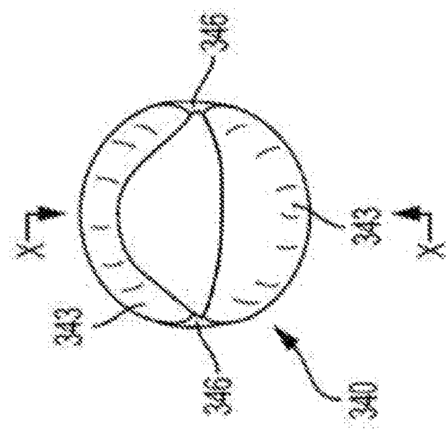
FIG. 3D

| | Name | Sequence | Position from start | Strand | Score | p-value | E-value |
|---|---|---|---|---|---|---|---|
| RunX2 | STAT5A | TGCCAGGAAAGGCCTTACCACAAG | 256 | + | 15 | 0 | 0 |
| | STAT5B | TTTCCTGGCATCC | 253 | - | 14.89 | 0.0001 | 0.049 |
| ACTA2 | STAT5B | CTTCCGGGAATTC | 227 | - | 18.8 | 0 | 0 |
| | STAT5B | ATTCCCGGAAGGG | 229 | + | 17.12 | 2.5E-05 | 0.0122 |
FIG. 15A
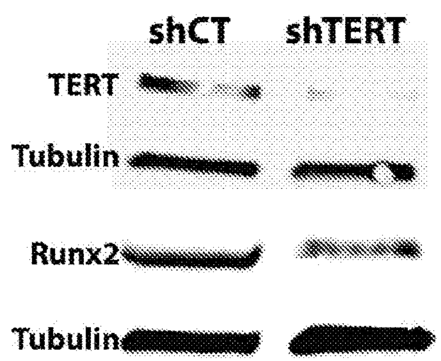
Fig. 15B
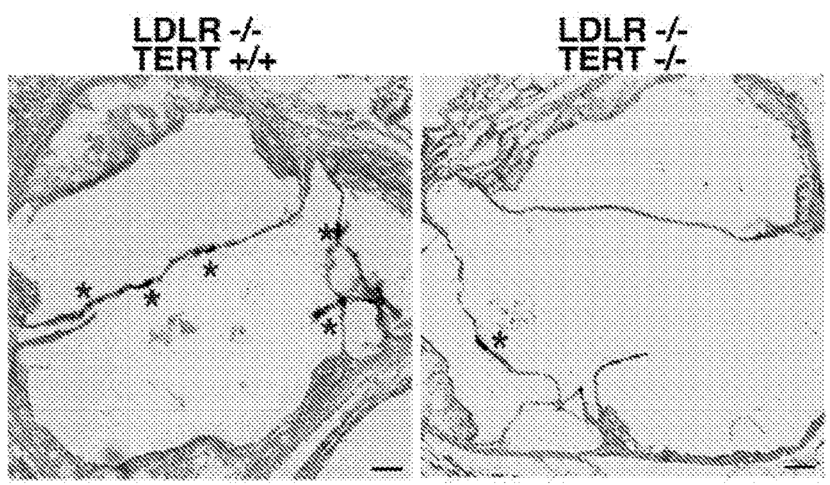
FIG. 16

SEQUENCE LISTING

```
<160> NUMBER OF SEQ ID NOS: 8

<210> SEQ ID NO 1
<211> LENGTH: 3829
<212> TYPE: DNA
```

<213> ORGANISM: Homo sapiens

<400> SEQUENCE: 1

```
caggcagcgc tgcgtcctgc tgcgcacgtg ggaagccctg gccccggcca cccccgcgat     60
gccgcgcgct ccccgctgcc gagccgtgcg ctccctgctg cgcagccact accgcgaggt    120
gctgccgctg gccacgttcg tgcggcgcct ggggccccag ggctggcggc tggtgcagcg    180
cggggacccg gcggctttcc gcgcgctggt ggcccagtgc ctggtgtgcg tgccctggga    240
cgcacggccg ccccccgccg ccccctcctt ccgccaggtg tcctgcctga aggagctggt    300
ggcccgagtg ctgcagaggc tgtgcgagcg cggcgcgaag aacgtgctgg ccttcggctt    360
cgcgctgctg gacggggccc gcgggggccc ccccgaggcc ttcaccacca gcgtgcgcag    420
ctacctgccc aacacggtga ccgacgcact gcgggggagc ggggcgtggg ggctgctgct    480
gcgccgcgtg ggcgacgacg tgctggttca cctgctggca cgctgcgcgc tctttgtgct    540
ggtggctccc agctgcgcct accaggtgtg cgggccgccg ctgtaccagc tcggcgctgc    600
cactcaggcc cggcccccgc cacacgctag tggaccccga aggcgtctgg gatgcgaacg    660
ggcctggaac catagcgtca gggaggccgg ggtcccccctg ggcctgccag ccccgggtgc    720
gaggaggcgc gggggcagtg ccagccgaag tctgccgttg cccaagaggc ccaggcgtgg    780
cgctgcccct gagccggagc ggacgcccgt tgggcagggg tcctgggccc acccgggcag    840
gacgcgtgga ccgagtgacc gtggtttctg tgtggtgtca cctgccagac ccgccgaaga    900
agccacctct ttggagggtg cgctctctgg cacgcgccac tcccacccat ccgtgggccg    960
ccagcaccac gcgggccccc catccacatc gcggccacca cgtccctggg acacgccttg   1020
tcccccggtg tacgccgaga ccaagcactt cctctactcc tcaggcgaca aggagcagct   1080
gcggccctcc ttcctactca gctctctgag gcccagcctg actggcgctc ggaggctcgt   1140
ggagaccatc tttctgggtt ccaggccctg gatgccaggg actccccgca ggttgccccg   1200
cctgccccag cgctactggc aaatgcggcc cctgtttctg gagctgcttg ggaaccacgc   1260
gcagtgcccc tacggggtgc tcctcaagac gcactgcccg ctgcgagctg cggtcacccc   1320
agcagccggt gtctgtgccc gggagaagcc ccagggctct gtggcggccc ccgaggagga   1380
ggacacagac ccccgtcgcc tggtgcagct gctccgccag cacagcagcc cctggcaggt   1440
gtacggcttc gtgcgggcct gcctgcgccg gctggtgccc ccaggcctct ggggctccag   1500
gcacaacgaa cgccgcttcc tcaggaacac caagaagttc atctccctgg ggaagcatgc   1560
caagctctcg ctgcaggagc tgacgtggaa gatgagcgtg cgggactgcg cttggctgcg   1620
caggagccca ggggttggct gtgttccggc cgcagagcac cgtctgcgtg aggagatcct   1680
ggccaagttc ctgcactggc tgatgagtgt gtacgtcgtc gagctgctca ggtctttctt   1740
ttatgtcacg gagaccacgt ttcaaaagaa caggctcttt ttctaccgga agagtgtctg   1800
gagcaagttg caaagcattg gaatcagaca gcacttgaag agggtgcagc tgcgggagct   1860
gtcggaagca gaggtcaggc agcatcggga agccaggccc gccctgctga cgtccagact   1920
ccgcttcatc cccaagcctg acgggctgcg gccgattgtg aacatggact acgtcgtggg   1980
agccagaacg ttccgcagag aaaagagggc cgagcgtctc acctcgaggg tgaaggcact   2040
gttcagcgtg ctcaactacg agcgggcgcg gcgccccggc ctcctgggcg cctctgtgct   2100
gggcctggac gatatccaca gggcctggcg caccttcgtg ctgcgtgtgc gggcccagga   2160
cccgccgcct gagctgtact ttgtcaaggt ggatgtgacg ggcgcgtacg acaccatccc   2220
ccaggacagg ctcacggagg tcatcgccag catcatcaaa ccccagaaca cgtactgcgt   2280
```

```
gcgtcggtat gccgtggtcc agaaggccgc ccatgggcac gtccgcaagg ccttcaagag   2340

ccacgtctct accttgacag acctccagcc gtacatgcga cagttcgtgg ctcacctgca   2400

ggagaccagc ccgctgaggg atgccgtcgt catcgagcag agctcctccc tgaatgaggc   2460

cagcagtggc ctcttcgacg tcttcctacg cttcatgtgc caccacgccg tgcgcatcag   2520

gggcaagtcc tacgtccagt gccaggggat cccgcagggc tccatcctct ccacgctgct   2580

ctgcagcctg tgctacggcg acatggagaa caagctgttt gcggggattc ggcgggacgg   2640

gctgctcctg cgtttggtgg atgatttctt gttggtgaca cctcacctca cccacgcgaa   2700

aaccttcctc agctatgccc ggacctccat cagagccagt ctcaccttca accgcggctt   2760

caaggctggg aggaacatgc gtcgcaaact ctttggggtc ttgcggctga agtgtcacag   2820

cctgtttctg gatttgcagg tgaacagcct ccagacggtg tgcaccaaca tctacaagat   2880

cctcctgctg caggcgtaca ggtttcacgc atgtgtgctg cagctcccat ttcatcagca   2940

agtttggaag aaccccacat tttcctgcg cgtcatctct gacacggcct ccctctgcta   3000

ctccatcctg aaagccaaga acgcagggat gtcgctgggg gccaagggcg ccgccggccc   3060

tctgccctcc gaggccgtgc agtggctgtg ccaccaagca ttcctgctca agctgactcg   3120

acaccgtgtc acctacgtgc cactcctggg gtcactcagg acagcccaga cgcagctgag   3180

tcggaagctc ccggggacga cgctgactgc cctggaggcc gcagccaacc cggcactgcc   3240

ctcagacttc aagaccatcc tggactgatg gccacccgcc cacagccagg ccgagagcag   3300

acaccagcag ccctgtcacg ccgggctcta cgtcccaggg agggaggggc ggcccacacc   3360

caggcccgca ccgctgggag tctgaggcct gagtgagtgt ttggccgagg cctgcatgtc   3420

cggctgaagg ctgagtgtcc ggctgaggcc tgagcgagtg tccagccaag ggctgagtgt   3480

ccagcacacc tgccgtcttc acttccccac aggctggcgc tcggctccac cccagggcca   3540

gcttttcctc accaggagcc cggcttccac tccccacata ggaatagtcc atccccagat   3600

tcgccattgt tcacccctcg ccctgccctc ctttgccttc cacccccacc atccaggtgg   3660

agaccctgag aaggaccctg ggagctctgg gaatttggag tgaccaaagg tgtgccctgt   3720

acacaggcga ggaccctgca cctggatggg ggtccctgtg ggtcaaattg gggggaggtg   3780

ctgtgggagt aaaatactga atatatgagt ttttcagttt tgaaaaaaa             3829
```

<210> SEQ ID NO 2
<211> LENGTH: 4018
<212> TYPE: DNA
<213> ORGANISM: Homo sapiens

<400> SEQUENCE: 2

```
caggcagcgc tgcgtcctgc tgcgcacgtg ggaagccctg gccccggcca cccccgcgat     60

gccgcgcgct ccccgctgcc gagccgtgcg ctccctgctg cgcagccact accgcgaggt    120

gctgccgctg gccacgttcg tgcggcgcct ggggccccag ggctggcggc tggtgcagcg    180

cggggacccg gcggctttcc gcgcgctggt ggcccagtgc ctggtgtgcg tgccctggga    240

cgcacggccg ccccccgccg ccccctcctt ccgccaggtg tcctgcctga aggagctggt    300

ggcccgagtg ctgcagaggc tgtgcgagcg cggcgcgaag aacgtgctgg ccttcggctt    360

cgcgctgctg gacggggccc gcgggggccc ccccgaggcc ttcaccacca gcgtgcgcag    420

ctacctgccc aacacggtga ccgacgcact gcgggggagc ggggcgtggg ggctgctgct    480

gcgccgcgtg ggcgacgacg tgctggttca cctgctggca cgctgcgcgc tctttgtgct    540
```

-continued

```
ggtggctccc agctgcgcct accaggtgtg cgggccgccg ctgtaccagc tcggcgctgc    600

cactcaggcc cggcccccgc cacacgctag tggaccccga aggcgtctgg gatgcgaacg    660

ggcctggaac catagcgtca gggaggccgg ggtccccctg ggcctgccag ccccgggtgc    720

gaggaggcgc gggggcagtg ccagccgaag tctgccgttg cccaagaggc ccaggcgtgg    780

cgctgcccct gagccggagc ggacgcccgt tgggcagggg tcctgggccc acccgggcag    840

gacgcgtgga ccgagtgacc gtggtttctg tgtggtgtca cctgccagac ccgccgaaga    900

agccacctct ttggagggtg cgctctctgg cacgcgccac tcccacccat ccgtgggccg    960

ccagcaccac gcgggccccc catccacatc gcggccacca cgtccctggg acacgccttg   1020

tcccccggtg tacgccgaga ccaagcactt cctctactcc tcaggcgaca aggagcagct   1080

gcggccctcc ttcctactca gctctctgag gcccagcctg actggcgctc ggaggctcgt   1140

ggagaccatc tttctgggtt ccaggccctg gatgccaggg actccccgca ggttgccccg   1200

cctgccccag cgctactggc aaatgcggcc cctgtttctg gagctgcttg ggaaccacgc   1260

gcagtgcccc tacggggtgc tcctcaagac gcactgcccg ctgcgagctg cggtcacccc   1320

agcagccggt gtctgtgccc gggagaagcc ccagggctct gtggcggccc ccgaggagga   1380

ggacacagac ccccgtcgcc tggtgcagct gctccgccag cacagcagcc cctggcaggt   1440

gtacggcttc gtgcgggcct gcctgcgccg gctggtgccc ccaggcctct ggggctccag   1500

gcacaacgaa cgccgcttcc tcaggaacac caagaagttc atctccctgg ggaagcatgc   1560

caagctctcg ctgcaggagc tgacgtggaa gatgagcgtg cgggactgcg cttggctgcg   1620

caggagccca ggggttggct gtgttccggc cgcagagcac cgtctgcgtg aggagatcct   1680

ggccaagttc ctgcactggc tgatgagtgt gtacgtcgtc gagctgctca ggtctttctt   1740

ttatgtcacg gagaccacgt ttcaaaagaa caggctcttt ttctaccgga agagtgtctg   1800

gagcaagttg caaagcattg gaatcagaca gcacttgaag agggtgcagc tgcgggagct   1860

gtcggaagca gaggtcaggc agcatcggga agccaggccc gccctgctga cgtccagact   1920

ccgcttcatc cccaagcctg acgggctgcg gccgattgtg aacatggact acgtcgtggg   1980

agccagaacg ttccgcagag aaaagagggc cgagcgtctc acctcgaggg tgaaggcact   2040

gttcagcgtg ctcaactacg agcgggcgcg gcgccccggc ctcctgggcg cctctgtgct   2100

gggcctggac gatatccaca gggcctggcg caccttcgtg ctgcgtgtgc gggcccagga   2160

cccgccgcct gagctgtact ttgtcaaggt ggatgtgacg ggcgcgtacg acaccatccc   2220

ccaggacagg ctcacggagg tcatcgccag catcatcaaa ccccagaaca cgtactgcgt   2280

gcgtcggtat gccgtggtcc agaaggccgc ccatgggcac gtccgcaagg ccttcaagag   2340

ccacgtctct accttgacag acctccagcc gtacatgcga cagttcgtgg ctcacctgca   2400

ggagaccagc ccgctgaggg atgccgtcgt catcgagcag agctcctccc tgaatgaggc   2460

cagcagtggc ctcttcgacg tcttcctacg cttcatgtgc caccacgccg tgcgcatcag   2520

ggccaagtcc tacgtccagt gccaggggat cccgcagggc tccatcctct ccacgctgct   2580

ctgcagcctg tgctacggcg acatggagaa caagctgttt gcggggattc ggcgggacgg   2640

gctgctcctg cgtttggtgg atgatttctt gttggtgaca cctcacctca cccacgcgaa   2700

aaccttcctc aggaccctgg tccgaggtgt ccctgagtat ggctgcgtgg tgaacttgcg   2760

gaagacagtg gtgaacttcc ctgtagaaga cgaggccctg ggtggcacgg cttttgttca   2820

gatgccggcc cacggcctat tcccctggtg cggcctgctg ctggataccc ggaccctgga   2880

ggtgcagagc gactactcca gctatgcccg gacctccatc agagccagtc tcaccttcaa   2940
```

```
ccgcggcttc aaggctggga ggaacatgcg tcgcaaactc tttggggtct tgcggctgaa   3000

gtgtcacagc ctgtttctgg atttgcaggt gaacagcctc cagacggtgt gcaccaacat   3060

ctacaagatc ctcctgctgc aggcgtacag gtttcacgca tgtgtgctgc agctcccatt   3120

tcatcagcaa gtttggaaga accccacatt tttcctgcgc gtcatctctg acacggcctc   3180

cctctgctac tccatcctga aagccaagaa cgcagggatg tcgctggggg ccaagggcgc   3240

cgccggccct ctgccctccg aggccgtgca gtggctgtgc caccaagcat tcctgctcaa   3300

gctgactcga caccgtgtca cctacgtgcc actcctgggg tcactcagga cagcccagac   3360

gcagctgagt cggaagctcc cggggacgac gctgactgcc ctggaggccg cagccaaccc   3420

ggcactgccc tcagacttca agaccatcct ggactgatgg ccacccgccc acagccaggc   3480

cgagagcaga caccagcagc cctgtcacgc cgggctctac gtcccaggga gggaggggcg   3540

gcccacaccc aggcccgcac cgctgggagt ctgaggcctg agtgagtgtt tggccgaggc   3600

ctgcatgtcc ggctgaaggc tgagtgtccg gctgaggcct gagcgagtgt ccagccaagg   3660

gctgagtgtc cagcacacct gccgtcttca cttccccaca ggctggcgct cggctccacc   3720

ccagggccag cttttcctca ccaggagccc ggcttccact ccccacatag gaatagtcca   3780

tccccagatt cgccattgtt cacccctcgc cctgccctcc tttgccttcc acccccacca   3840

tccaggtgga gaccctgaga aggaccctgg gagctctggg aatttggagt gaccaaaggt   3900

gtgccctgta cacaggcgag gaccctgcac ctggatgggg gtccctgtgg gtcaaattgg   3960

ggggaggtgc tgtgggagta aaatactgaa tatatgagtt tttcagtttt gaaaaaaa     4018
```

<210> SEQ ID NO 3
<211> LENGTH: 1132
<212> TYPE: PRT
<213> ORGANISM: Homo sapiens

<400> SEQUENCE: 3

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
```

-continued

```
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605
```

```
His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn  Ile Tyr Lys Ile Leu  Leu Leu Gln
        995                 1000                1005

Ala Tyr  Arg Phe His Ala Cys  Val Leu Gln Leu Pro  Phe His Gln
    1010                1015                1020
```

-continued

```
Gln Val  Trp Lys Asn Pro Thr  Phe Phe Leu Arg Val  Ile Ser Asp
    1025                 1030                 1035

Thr Ala  Ser Leu Cys Tyr Ser  Ile Leu Lys Ala Lys  Asn Ala Gly
    1040                 1045                 1050

Met Ser  Leu Gly Ala Lys Gly  Ala Ala Gly Pro Leu  Pro Ser Glu
    1055                 1060                 1065

Ala Val  Gln Trp Leu Cys His  Gln Ala Phe Leu Leu  Lys Leu Thr
    1070                 1075                 1080

Arg His  Arg Val Thr Tyr Val  Pro Leu Leu Gly Ser  Leu Arg Thr
    1085                 1090                 1095

Ala Gln  Thr Gln Leu Ser Arg  Lys Leu Pro Gly Thr  Thr Leu Thr
    1100                 1105                 1110

Ala Leu  Glu Ala Ala Ala Asn  Pro Ala Leu Pro Ser  Asp Phe Lys
    1115                 1120                 1125

Thr Ile  Leu Asp
    1130


<210> SEQ ID NO 4
<211> LENGTH: 24
<212> TYPE: DNA
<213> ORGANISM: Homo sapiens

<400> SEQUENCE: 4

tgccaggaaa ggccttacca caag                                        24


<210> SEQ ID NO 5
<211> LENGTH: 13
<212> TYPE: DNA
<213> ORGANISM: Homo sapiens

<400> SEQUENCE: 5

tttcctggca tcc                                                    13


<210> SEQ ID NO 6
<211> LENGTH: 13
<212> TYPE: DNA
<213> ORGANISM: Homo sapiens

<400> SEQUENCE: 6

cttccgggaa ttc                                                    13


<210> SEQ ID NO 7
<211> LENGTH: 13
<212> TYPE: DNA
<213> ORGANISM: Homo sapiens

<400> SEQUENCE: 7

attcccggaa ggg                                                    13


<210> SEQ ID NO 8
<211> LENGTH: 19
<212> TYPE: DNA
<213> ORGANISM: Artificial Sequence
<220> FEATURE:
<223> OTHER INFORMATION: humanTERT shRNA

<400> SEQUENCE: 8

tgctcaggtc tttctttta                                              19
```

GENETICALLY MODIFIED MESENCHYMAL STEM CELLS FOR USE IN CARDIOVASCULAR PROSTHETICS

CROSS REFERENCE TO RELATED APPLICATIONS

This application is the United States national phase of International Application No. PCT/US2018/055908 filed Oct. 15, 2018, and claims the benefit of U.S. Provisional Patent Application No. 62/572,709, filed Oct. 16, 2017, each of which is incorporated herein by reference in its entirety.

SEQUENCE LISTING

The Sequence Listing associated with this application is filed in electronic format via EFS-Web and is hereby incorporated by reference into the specification in its entirety. The name of the text file containing the Sequence Listing is 6527_2001684_ST25.txt. The size of the text file is 21,309 bytes, and the text file was created on Apr. 6, 2020.

A cardiovascular graft is provided. Methods of making and using the cardiovascular graft also is provided.

Calcification of the aortic valve, broadly called calcific aortic valve disease (CAVD), is common in the aging population, with close to 30% of individuals over 60 years old presenting with CAVD. The term CAVD describes a spectrum from aortic sclerosis, the thickening and stiffening of the valve leaflets, to aortic stenosis, where blood flow to the aorta is obstructed and can lead to heart failure. CAVD causes serious medical and financial burden with current annual costs estimated to be $31 billion. In addition to age-related development of CAVD, roughly 1-2% of the population harbors congenital malformations of bicuspid or unicuspid aortic valves; these malformed valves are prone to calcify and many of these individuals develop CAVD. Currently there is no treatment that halts or reverses pathologic calcification, and the mortality rate of untreated severe aortic stenosis reaches 50% within 2-3 years.

Current options for valve replacements are mechanical valves or valves created from fixed biologically-derived soft tissues, called bioprosthetic heart valves (BHVs). Mechanical valves are durable but are prone to infection and alter blood-flow patterns, which greatly increases the risk of thrombogenic events, thus patients require life-long anticoagulation therapy which has its own associated risks. BHVs are decellularized valves obtained from bovine or porcine sources that are then combined with the endogenous valves of the patient or pericardium tissue. BHVs provide greater functionality and are much less thrombogenic, however these valves will develop calcification and eventually fail. It is therefore desirable to have a method and tissue engineered heart valve prosthetics that are not prone to calcification.

SUMMARY

In one aspect, a method of preparing a cardiovascular graft is provided. The method comprises seeding a bioerodible cell growth scaffold with mesenchymal stem cells (MSCs), such as human MSCs, that are modified to reduce or eliminate expression or activity of telomerase reverse transcriptase (TERT).

In another aspect, a cardiovascular graft is provided. The cardiovascular graft comprises mesenchymal stem cells (MSCs), such as human MSCs, modified to reduce or eliminate expression or activity of telomerase reverse transcriptase (TERT) or cells differentiated from the modified MSCs modified to reduce or eliminate expression or activity of TERT.

In another aspect, a method of treating a cardiovascular defect or injury in a patient is provided. The method comprises implanting or depositing at a site of a defect or injury in a patient, a cardiovascular graft comprising mesenchymal stem cells (MSCs), such as human MSCs, modified to reduce or eliminate expression or activity of telomerase reverse transcriptase (TERT) or cells differentiated from the modified MSCs modified to reduce or eliminate expression or activity of TERT.

BRIEF DESCRIPTION OF THE DRAWINGS

FIG. 1 (extending continuously from FIG. 1-1 to FIG. 1-3) provides non-limiting examples of TERT mRNA and protein sequences, including: telomerase reverse transcriptase isoform 2: NM_001193376.1 (SEQ ID NO: 1), and telomerase reverse transcriptase isoform 1: NM_198253.2 (SEQ ID NO: 2) and NP_937983.2 (SEQ ID NO: 3).

FIGS. 3A-3E depict schematically aspects of a prosthetic bicuspid valve.

FIG. 10 provides graphs showing that telomere length is not different between healthy and CAVD VICs, and that the ages of the patient cohort is similar.

FIG. 15A provides sequences of STAT5 binding sites in Runx2 (SEQ ID NOS: 4 and 5) and SMA-α (ACTA2 (SEQ ID NOS: 6 and 7)). FIG. 15B is a photograph of a western blot showing that reducing expression of TERT reduces the expression of the osteogenic protein Runx2.

FIG. 16 provides photomicrographs showing that genetic deletion of TERT reduces valve calcification in vivo. Scale bar, 100 um.

DETAILED DESCRIPTION

Figure 2:
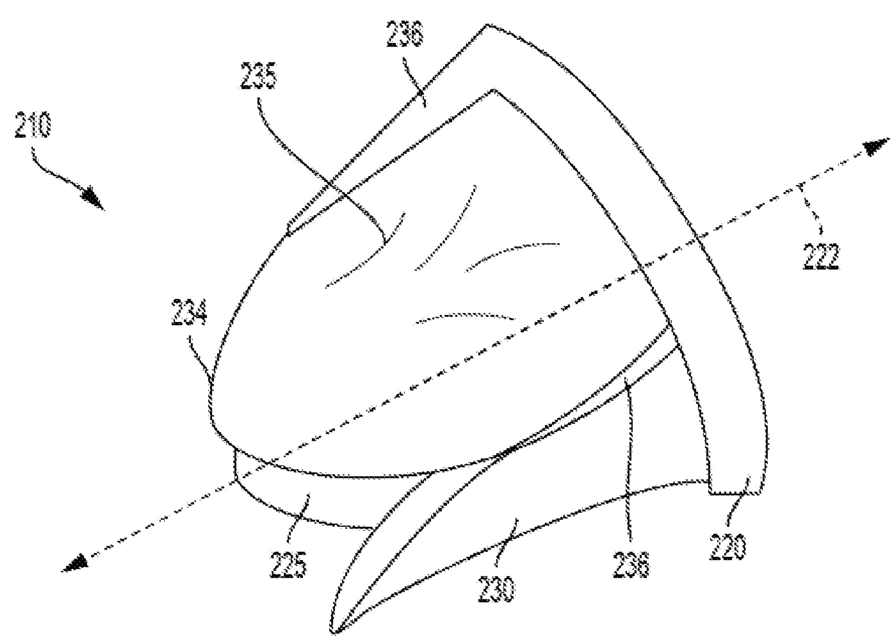
FIG. 2 depicts schematically aspects of a prosthetic tricuspid valve.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

As used herein, the terms "right", "left", "top", "bottom", and derivatives thereof shall relate to the invention as it is oriented in the drawing Figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

As used herein, the terms "comprising," "comprise" or "comprised," and variations thereof, are meant to be open ended. The terms "a" and "an" are intended to refer to one or more.

In one aspect, a heart valve prosthetic and related methods are described herein, whereby a bioerodible (bioabsorbable) scaffold is seeded with autologous cells that have been isolated from the patient and cultured in vitro. Mesenchymal stem cells are multipotent progenitor cells that can be obtained readily from the bone marrow or adipose tissues and have been successfully used to seed a bioabsorbable scaffold that was implanted into an ovine model which survived for 4 months. As described herein, the protein telomerase reverse transcriptase (TERT) is highly expressed in human mesenchymal stem cells that are calcifying, in CAVD valve tissues, and in valve interstitial cells isolated from patient CAVD valves. By knocking down TERT expression, levels of the transcription factor RUNX2, a master regulator of osteogenesis, are reduced. Genetic deletion of TERT in a vascular smooth muscle cell prevents calcification in vitro. Based on this, a superior tissue-engineered valve is described whereby autologous mesenchymal stem cells are isolated from patients, genetically modified ex vivo to knock out or knock down TERT, seeded on a bioerodible scaffold that is optionally cultured in vitro, and then implanted into a patient. This is expected to produce a tissue-engineered heart valve that is more resistant to calcification than current heart valve replacements, such as BHV replacements. Effective seeding of prosthetic heart valves is described in the literature (see, e.g., VeDepo, M C, et al. "Recellularization of decellularized heart valves: Progress toward the tissue-engineered heart valve" (2017) *J. Tissue Eng.* 8:1-21; Jana, S., et al. "Cells for tissue engineering of cardiac valves" *J Tissue Eng Regen Med.* (2016) 10(10):804-824; and U.S. Pat. No. 6,387,369).

As used herein, the "treatment" or "treating" of a condition, wound, or defect means administration to a patient by any suitable dosage regimen, procedure and/or administration route of a composition, device or structure with the object of achieving a desirable clinical/medical end-point, including repair and/or replacement of a damaged, defective, or malformed tricuspid or mitral (bicuspid) valve.

The term "patient" or "subject" refers to members of the animal kingdom including but not limited to human beings and "mammal" refers to all mammals, including, but not limited to human beings.

A polymer composition is "biocompatible" in that the polymer and, where applicable, degradation products thereof, are substantially non-toxic to cells or organisms within acceptable tolerances, including substantially non-carcinogenic and substantially non-immunogenic, and are cleared or otherwise degraded in a biological system, such as an organism (patient) without substantial toxic effect. Non-limiting examples of degradation mechanisms within a biological system include chemical reactions, hydrolysis reactions, and enzymatic cleavage.

As used herein, the term "polymer composition" is a composition comprising one or more polymers. As a class, "polymers" includes, without limitation, homopolymers, heteropolymers, co-polymers, block polymers, block co-polymers and can be both natural and/or synthetic. Homopolymers contain one type of building block, or monomer, whereas copolymers contain more than one type of monomer. The term "(co)polymer" and like terms refer to either homopolymers or copolymers.

A polymer "comprises" or is "derived from" a stated monomer if that monomer is incorporated into the polymer. Thus, the incorporated monomer (monomer residue) that the polymer comprises is not the same as the monomer prior to incorporation into a polymer, in that at the very least, certain groups are missing and/or modified when incorporated into the polymer backbone. A polymer is said to comprise a specific type of linkage if that linkage is present in the polymer as a consequence of its normal or intended polymerization and/or cross-linking processes.

As described herein, a "fiber" is an elongated, slender, thread-like and/or filamentous structure. A "matrix" is any two- or three-dimensional arrangement of elements (e.g., fibers), either ordered (e.g., in a woven or non-woven mesh) or randomly-arranged (as is typical with a mat of fibers typically produced by electrospinning) and can be isotropic or anisotropic.

By "biodegradable or "bioerodible", it is meant that a material, such as a polymer, once implanted and placed in contact with bodily fluids and tissues, will degrade either partially or completely through chemical reactions with the bodily fluids and/or tissues, typically and often preferably over a time period of hours, days, weeks or months. Non-limiting examples of such chemical reactions include acid/base reactions, hydrolysis reactions, and enzymatic cleavage. The biodegradation rate of the polymer matrix may be manipulated, optimized or otherwise adjusted so that the matrix degrades over a useful time period. Bioerodible polymers degrade in vivo over a time period. "Non-bioerodible" polymers (e.g., durable polymers) do not degrade to any significant extent in vivo over a time period of at least two years, for instance, they do not degrade substantially in vivo in five or ten years, and include polyethylene terephthalate (PET, including DACRON®) and PTFE (polytetrafluoroethylene, including expanded PTFE (ePTFE, W. L. Gore), and TEFLON®), which are often used in implantable medical devices. Other non-limiting examples of non-bioerodible polymers include: poly(ethylene-co-vinyl acetate), poly(n-butyl methacrylate), and poly(styrene-b-isobutylene-b-styrene).

A "cell growth scaffold", "cell growth matrix", or the like, is a porous matrix of one or more compositions suitable as a substrate for cell growth, and typically allow for cell population expansion, cell differentiation, and/or cell infiltration into the matrix. The matrix of the scaffold is prepared from natural and/or synthetic polymeric materials, for example the ECM materials and/or the synthetic polymers described below, and may be bioerodible or non-bioerodible. Cell growth scaffolds can be prepared by any suitable method for production of porous compositions, such as, without limitation, by molding with a dissolvable porogen or electrodeposition, and methods for preparing cell growth scaffolds are broadly-known to those of ordinary skill.

As used herein, "reagent" when used in the context of an antisense, RNAi, short hairpin RNA (shRNA), or ribozyme, or other single-stranded or double-stranded RNA interfering nucleic acids, refers not only to RNA structures, but effective nucleic acid analog structures. In antisense and RNAi technologies, use of RNA poses significant delivery issues due to the lability of RNA molecules. As such, RNA is commonly chemically-modified to produce nucleic acid analogs, not only to enhance stability of the nucleic acid molecules, but often resulting in increased binding affinity, and with reduced toxicity. Such modifications are broadly-known to those of ordinary skill in the art, and are available commercially (see, e.g., Corey, D. R., Chemical modification: the key to clinical application of RNA interference? (2007) *J Clin Invest.* 117(12):3615-3622, also describing RNAi, and United States Patent Publication No. 20170081667). Non-limiting examples of modifications to the nucleic acid structure in nucleic acid analogs include: modifications to the phosphate linkage, such as phosphoramidates or phosphorothioates; sugar modification, such as 2'-O, 4'-C methylene bridged, locked nucleic acid (LNA), 2'-methoxy, 2'-O-methoxyethyl (MOE), 2'-fluoro, S-constrained-ethyl (cEt), and tricyclo-DNA (tc-DNA); and non-ribose structures, such as phosphorodiamidate morpholino (PMO), and peptide-nucleic acids (PNA).

A "binding reagent" is a reagent, compound or composition, e.g., a ligand, able to specifically bind a target compound, such as TERT or a member of the TERT interactome. A binding reagent can interfere with TERT activity, for example as an antagonist or decoy within the pathway of TERT's osteogenic activity. An "interactome" is the set of molecular interactions in a cell, such as in an MSC, and includes, for example and without limitation, protein-protein interactions and protein-nucleic acid interactions, e.g., within the pathway directing TERT's osteogenic activity. Binding reagents include, without limitation, antibodies (polyclonal, monoclonal, humanized, etc.), antibody fragments (e.g., a recombinant scFv), antibody mimetics such as affibodies, affilins, affimers, affitins, alphabodies, anticalins, avimers, DARPins, fynomers, monobodies, nucleic acid ligands (e.g., aptamers), engineered proteins, antigens, epitopes, haptens, or any target-specific binding reagent. In aspects, binding reagents includes as a class: monoclonal antibodies, or derivatives or analogs thereof, including without limitation: Fv fragments, single chain Fv (scFv) fragments, Fab' fragments, $F(ab')_2$ fragments, single domain antibodies, camelized antibodies and antibody fragments, humanized antibodies and antibody fragments, multivalent versions of the foregoing, and any paratope-containing compound or composition; multivalent activators including without limitation: monospecific or bispecific antibodies, such as disulfide stabilized Fv fragments, scFv tandems ($(scFv)_2$ fragments), diabodies, tribodies or tetrabodies, which typically are covalently linked or otherwise stabilized (i.e., leucine zipper or helix stabilized) scFv fragments; nucleic acids and analogs thereof that bind a target compound; or receptor molecules which naturally interact with a desired target molecule.

By "target-specific" or reference to the ability of one compound to bind another target compound specifically, it is meant that the compound binds to the target compound to the exclusion of others in a given reaction system, e.g., in vitro, or in vivo, to acceptable tolerances, permitting a sufficiently specific diagnostic or therapeutic effect according to the standards of a person of skill in the art, a medical community, and/or a regulatory authority, such as the U.S. Food and Drug Agency (FDA). In aspects, in the context of targeting TERT, and down-regulating TERT activity, the therapeutic effect may be binding TERT, or a member of the TERT interactome, to safely and effectively reduce heart valve calcification in cells derived from MSCs as described herein.

Cells may be differentiated and/or progenitor cells. Cells progress (differentiate) through lineage beginning from progenitor cells, such as stem cells, including pluripotent cells, and along a lineage of multipotent progenitor cells, oligopotent progenitor cells, to a unipotent cells, or terminally differentiated cells. Mesenchymal stem cells (MSCs) are multipotent progenitor cells found in adult tissue, including, without limitation, bone marrow, umbilical cord blood, muscle, and adipose tissue. Adipose tissue is a generous source of MSCs, and can be readily obtained from a patient by lipoaspiration (e.g., liposuction).

In one aspect, and without limitation, MSCs can be obtained from adipose tissue according to the following: lipoaspirated adipose tissue is collected and washed, e.g., in saline. The tissue is then centrifuged or settled to separate the tissue from free lipids and from aqueous wash. The adipose tissue is then treated with a proteinase, such as collagenase, to dissolve the extracellular matrix (ECM), and to release individual cells. Alternatively, and avoiding enzymatic digestion, the fat tissue can be vibrated (e.g., 6000 vibrations per minute) to release cells from the tissue. The digest or shaken tissue optionally can be filtered. The tissue is then centrifuged to separate the stromal vascular fraction (SVF), comprising adipose-derived stem cells, from adipocytes (see, e.g., Rasposio, E, et al. "Adipose-derived stem cells: Comparison between two methods of isolation for clinical applications" *Ann Med Surg* (Lond) 2017 August; 20: 87-91).

The SVF can be used directly as an enriched source of MSCs, or can be cultured and optionally stored. MSCs are among cells in the SVF that adhere to plastic, such as a typical tissue culture dish or flask. As such, the cells may be cultured for a suitable time in suitable medium to support growth of the MSCs (available, e.g., commercially, e.g., MESENCULT™ products, from Stem Cell Technologies, Inc. of Cambridge, Mass.), and the enriched MSC population is cultured under non-differentiation conditions. MSCs can be removed from the culture vessel by typical tissue culture methods, and can be seeded on a suitable growth scaffold, such as a heart valve prosthesis or a blood vessel prosthesis, made from synthetic and/or natural polymeric material, that can be bioerodible, and cultured under conditions supporting in-growth of the cells and differentiation of the cells to, e.g., valve interstitial cells, and endothelial cells, such as valve endothelial cells or vascular endothelial cells, in differentiation medium, such as: for endothelial cells, Endothelial Cell Growth Medium MV2 from PromoCell GmbH of Heidelberg, Germany (cat# C-22022), or, for fibroblasts or interstitial cells, Fibroblast Growth Medium 3 from PromoCell (cat# C-23025).

A "gene" is a sequence of DNA or RNA which codes for a molecule, such as a protein or a functional RNA that has a function. Nucleic acids are biopolymers, or small biomolecules, essential to all known forms of life. They are composed of nucleotides, which are monomers made of three components: a 5-carbon sugar, a phosphate group and a nitrogenous base. If the sugar is a simple ribose, the polymer is RNA; if the sugar is derived from ribose as deoxyribose, the polymer is DNA. DNA uses the nitrogenous bases guanine, thymine, adenine, and cytosine. RNA uses the nitrogenous bases guanine, uracil, adenine, and cytosine.

"Complementary" refers to the ability of polynucleotides (nucleic acids) to hybridize to one another, forming inter-strand base pairs. Base pairs are formed by hydrogen bonding between nucleotide units in antiparallel polynucleotide strands. Complementary polynucleotide strands can base-pair (hybridize) in the Watson-Crick manner (e.g., A to T, A to U, C to G), or in any other manner that allows for the formation of duplexes. When using RNA as opposed to DNA, uracil, rather than thymine, is the base that is considered to be complementary to adenosine. Two sequences comprising complementary sequences can hybridize if they form duplexes under specified conditions, such as in water, saline (e.g., normal saline, or 0.9% w/v saline) or phosphate-buffered saline), or under other stringency conditions, such as, for example and without limitation, 0.1×SSC (saline sodium citrate) to 10×SSC, where 1×SSC is 0.15M NaCl and 0.015M sodium citrate in water. Hybridization of complementary sequences is dictated, e.g., by salt concentration and temperature, with the melting temperature (Tm) lowering with increased mismatches and increased stringency. Perfectly matched sequences are said to be fully complementary, or have 100% sequence identity (gaps are not counted and the measurement is in relation to the shorter of the two sequences). In one aspect, a sequence that "specifically hybridizes" to another sequence, does so in a hybridization solution containing 0.5M sodium phosphate buffer, pH 7.2, containing 7% SDS, 1 mM EDTA, and 100 mg/ml of salmon sperm DNA at 65° C. for 16 hours, and washing twice at 65° C. for twenty minutes in a washing solution containing 0.5×SSC and 0.1% SDS, or does so under conditions more stringent than 2×SSC at 65° C., for example, in 0.2×SSC at 55° C. A sequence that specifically hybridizes to another typically has at least 80%, 85%, 90%, 95%, OR 99% sequence identity with the other sequence. As used herein, "sequence identity" refers to the extent to which two (nucleotide or amino acid) sequences have the same residues at the same positions in an alignment, often expressed as a percentage. Gaps are not counted and the measurement is related to the shorter of the two sequences.

Gene expression is the process by which information from a gene is used in the synthesis of a functional gene product, e.g., a protein or functional RNA. Gene expression involves various steps, including transcription, translation, and post-translational modification of a protein.

Transcription is the process by which the DNA gene sequence is transcribed into pre-mRNA (messenger RNA). The steps include: RNA polymerase, together with one or more general transcription factors, binds to promoter DNA. Transcription factors (TFs) are proteins that control the rate of transcription of genetic information from DNA to messenger RNA, by binding to a specific DNA sequence (i.e., the promoter region). The function of TFs is to regulate genes in order to make sure that they are expressed in the right cell at the right time, and in the right amount, throughout the life of the cell and the organism. The promoter region of a gene is a region of DNA that initiates transcription of that particular gene. Promoters are located near the transcription start sites of genes, on the same strand, and often, but not exclusively, are upstream (towards the 5' region of the sense strand) on the DNA. Promoters can be about 100-1000 base pairs long. Additional sequences and non-coding elements can affect transcription rates. If the cell has a nucleus (eukaryotes), the RNA is further processed. This includes polyadenylation, capping, and splicing. Polyadenylation is the addition of a poly(A) tail to a messenger RNA. The poly(A) tail consists of multiple adenosine monophosphates. In eukaryotes, polyadenylation is part of the process that produces mature messenger RNA (mRNA) for translation. Capping refers to the process wherein the 5' end of the pre-mRNA has a specially altered nucleotide. In eukaryotes, the 5' cap (cap-0), found on the 5' end of an mRNA molecule consists of a guanine nucleotide connected to mRNA via an unusual 5' to 5' triphosphate linkage. During RNA splicing, pre-mRNA is edited. Specifically, during this process introns are removed and exons are joined together. The resultant product is known as mature mRNA. The RNA may remain in the nucleus or exit to the cytoplasm through the nuclear pore complex.

RNA levels in a cell, e.g., mRNA levels, can be controlled post-transcriptionally. Native mechanisms, including: endogenous gene silencing mechanisms, interference with translational mechanisms, interference with RNA splicing mechanisms, and destruction of duplexed RNA by RNAse H, or RNAse H-like, activity. As is broadly-recognized by those of ordinary skill in the art, these endogenous mechanisms can be exploited to decrease or silence mRNA activity in a cell or organism in a sequence-specific, targeted manner. Antisense technology typically involves administration of a single-stranded antisense oligonucleotide (ASO) that is chemically-modified, e.g., as described herein, for bio-stability, and is administered in sufficient amounts to effectively penetrate the cell and bind in sufficient quantities to target mRNAs in cells. RNA interference (RNAi) harnesses an endogenous and catalytic gene silencing mechanism, which means that once, e.g., a microRNA, or double-stranded siRNA (small interfering RNA) has been delivered, for example, by endogenous production via a gene for expressing the silencing RNA, they are efficiently recognized and stably incorporated into the RNA-induced silencing complex (RISC) to achieve prolonged gene silencing. Both antisense technologies and RNAi have their strengths and weaknesses, either may be used effectively to knock-down, decrease, or silence expression of a gene, such as TERT (see, e.g., Watts, J. K., et al. Gene silencing by siRNAs and antisense oligonucleotides in the laboratory and the clinic (2012) 226(2):365-379).

During translation, mRNA is decoded in a ribosome, outside the nucleus, to produce a specific amino acid chain, or polypeptide. A codon refers to a sequence of three nucleotides. The information for protein synthesis is the form of these three-nucleotide codons, which each specify one amino acid. The protein coding regions of each mRNA is composed of a contiguous, non-overlapping string of codons called an open-reading frame (ORF). Each ORF specifies a single protein and starts and ends at internal sites within the mRNA. Translation starts at the 5' end of the ORF and proceeds one codon at a time to the 3' end. The first and last codons of an ORF are known as the "start" and "stop"

codons. Polycistronic mRNAs are mRNAs containing multiple ORFs, and those mRNAs encoding a single ORF are known as monocistronic mRNAs.

Translation proceeds in three phases: initiation, elongation and termination. For translation to occur, the ribosome must be recruited to the mRNA. To facilitate binding by a ribosome, many prokaryotic ORFs contain a short sequence upstream of the start codon called the ribosome binding site (RBS), also known as the Shine-Dalgarno sequence. This area of the mRNA that is upstream of the start codon is known as the 5' untranslated region (UTR), and is also known as a leader sequence or leader RNA. In eukaryotes, the 5' cap assists in ribosome binding during translation, among other roles. Additionally, the presence of a Kozak sequence (a purine three bases upstream of the start codon and a guanine immediately downstream) helps increase the efficiency of translation. During elongation, the ribosome catalyzes sequential additions of aminoacyl-tRNA corresponding to codons of the ORF of the mRNA, and transfers amino acids to the nascent polypeptide, based on the sequence of codons. The ribosome then moves to the next mRNA codon to continue the process, creating an amino acid chain. In termination of translation, a stop codon is reached, at which point, translation ceases. The nascent polypeptide can then be post-translationally modified, wherein chemical modifications are added, e.g., to the C- or N-termini of the polypeptide.

In aspects, by "decreasing TERT activity", "Knocking down TERT activity", "Knocking out TERT activity", or "downregulating TERT activity", it is meant any action or modification that results in lower activity of TERT in a cell or patient—typically by use of a therapeutic agent, by transient gene introduction into the cell, e.g., via episomal DNA, or by genetic modification of genomic DNA, for example and without limitation, by incorporating a gene for expressing an interfering RNA into a genome of a cell, e.g., an MSC, or by editing the TERT gene so that expression thereof is lowered or stopped, for example, by adding a stop codon into the ORF of the TERT gene. Useful therapeutic agents include, without limitation, antisense, ribozyme of RNA interference (RNAi) compositions; binding reagents, such as antibodies (including antibody fragments or antibody-based polypeptide ligands), and aptamers; antagonists; decoys; and peptide-based therapies. As would be recognized by one of ordinary skill, there are a multitude of systems either available commercially or described in publications, useful for gene transfer, gene editing, or otherwise knocking down, knocking out, reducing, or silencing expression or activity of TERT.

In one aspect, the decreasing of TERT activity is non-transient, meaning that the cell, e.g., a MSC, is modified, e.g., genetically-modified, either to knock out the TERT gene, or to knock down expression from the TERT gene at the transcriptional, post-transcriptional, or translational level, such as by introducing a stop codon into the ORF of one or both alleles of the TERT gene by CRISPR/CAS9 technology, or other gene editing technologies. In another aspect, the cell, e.g., MSC, is genetically-modified to produce a reagent that knocks down expression of TERT, for instance, by production of an siRNA, an antisense reagent, a ribozyme, or a binding reagent, such as an antibody or scFv, that otherwise binds TERT or a member of the TERT interactome, or otherwise interferes with TERT function, e.g., TERT's osteogenic function. In one aspect, TERT is silenced by RNA interference (RNAi), which utilizes endogenous RNA interference pathway to process shRNA (short hairpin RNA) using Dicer, for generation of siRNA or miRNA for activation of the RNA-induced silencing complex (RISC), as is broadly-known. Typically small interfering RNAs (siRNAs) are used for RNA interference, e.g., as generated by those commercially-available shRNA constructs identified below. Identifying useful sequences for production of siRNAs is within the skill of an ordinary artisan, e.g., through use of design rules, e.g., algorithms for implementation on a computer, for designing siRNAs for use in gene silencing (see, e.g., Birmingham, A., et. al., "A protocol for designing siRNAs with high functionality and specificity," *Nature Methods*, August 2007; 9: 2068-2078). In one example, an shRNA for knocking down expression of TERT has the sequence: TGCTCAGGTCTTTCTTTTA (SEQ ID NO: 8). This is merely one example of the many identified or readily-identifiable siRNA sequences for human TERT. For example, in reference to GenBank Accession No. NM_001193376.1 (SEQ ID NO: 1), ThermoFisher Scientific identifies siRNA targets at locations 1757, 1731, 1049, 1538, 285, 1532, 1739, 1781, 2055, 2101, 2830, 2813, 2294, 1585, and 1760. Commercially-available RNAi products that target various sequences within the TERT sequence (e.g., NM_001193376.1 (SEQ ID NO: 1)), including siRNA and shRNA-expressing vectors, are available from a number of other companies. For example, Dharmacon of Lafayette Colo. offers a large number of siRNA reagents and sRNA-producing inducible vectors directed to human TERT.

Genes (transgenes) can be introduced into, and incorporated into the genome of cells, such as MSCs, by a variety of mechanisms, including by direct DNA transfer, genome editing, or viral vector-directed integration.

In the case of viruses for transgene expression, various vector systems have been developed with cloning vectors being available either commercially or from the research community, and which are broadly disclosed in publications and patent documents over the last few decades, with adenovirus (Ad), adeno-associated virus (AAV), lentivirus, and γ-retrovirus vectors being exemplary and common. In use, recombinant viral genomes including the gene to be transferred are packaged into recombinant viral transducing particle, which are then used to modify a cell, such as an MSC.

Adenoviruses are a class of medium-sized, non-enveloped, double-stranded DNA viruses known to cause mild to severe respiratory disease in humans. Advantages of adenoviruses in research include their large packaging capacity (>8 kb), high titers, and high levels of transgene expression. Additionally, these viruses are able to target a broad range of dividing and non-dividing cell types with almost 100% efficiency. Unlike lentiviruses or other retroviruses, adenoviruses do not integrate into the host genome. Disadvantages of adenoviruses include transient transgene expression, as well as the substantial immune response induced by the viral capsid. Adenoviruses can be produced by several methods, the most common of which involves homologous recombination of adenovirus plasmids in either mammalian cells or microorganisms, including bacteria and yeast. Two plasmids, termed a shuttle plasmid and an adenoviral (also called backbone) plasmid, are recombined into a DNA molecule that incorporates sequences from both plasmids. This DNA molecule can then be transfected into mammalian packaging cell lines to generate adenovirus particles.

Lentiviruses, a subset of retroviruses, are some of the most common and useful types of viruses used in research. Lentivirus can transduce both dividing and non-dividing cells without a significant immune response. These viruses also integrate stably into the host genome, enabling long term transgene expression. There are some safety considerations to evaluate when working with lentivirus: these viruses are based on HIV-1, which may require additional lab biosafety procedures. Additionally, because this virus integrates randomly into the host genome, it has the potential for insertional mutagenesis.

Adeno-associated viruses (AAV) are small viruses originally discovered as contaminants of adenovirus stocks. One major advantage of using AAV for research is that it is replication-limited and typically not known to cause disease in humans. For these reasons, AAVs are generally contained at lower biosafety levels and elicit relatively low immunological effects in vivo. AAV can transduce both dividing and non-dividing cells with a low immune response and low toxicity. Although recombinant AAV does not readily integrate into the host genome, transgene expression can be long-lived. The utility of AAV is currently limited by its small packaging capacity (~4.5 kb including ITRs), though there is a great deal of interest and effort directed toward expanding this capacity. Traditionally, AAV requires the presence of another "helper" virus, such as adenovirus or herpes virus, in order to propagate. This is due to the reliance of the AAV on certain exogenous gene products that mediate AAV replication. This requirement has been circumvented with "helper-virus free systems," which enable the production of infectious AAV particles without the use of a helper virus. Instead, specific gene products can be provided by helper plasmids (e.g., pHelper) and specific packaging cell lines (e.g., HEK293 cells) during AAV production. See, e.g., Kotterman, M. A. et al. "Engineering adeno-associated viruses for clinical gene therapy" (2014) *Nat Rev Genet* 15,445-451.

γ-Retrovirus (gamma-retrovirus) is an RNA virus comprised of its genome and several structural and enzymatic proteins, including reverse transcriptase and integrase. Once in a target cell, the virus uses the reverse transcriptase in tow to generate a DNA provirus. This provirus then gets integrated into the host's genome by the accompanying integrase protein. γ-Retroviruses can package relatively high amounts of DNA (up to ~8 kb), and infection results in long-term transgene expression. Some disadvantages of γ-retroviruses are that they can only transduce dividing cells (this is because they are only able to enter the nucleus during mitotic breakdown of the nuclear envelope). Additionally, γ-retroviruses integrate randomly into the host's genome, which can lead to oncogenesis (termed insertional mutagenesis).

Genome editing is another method by which expression of a gene can be reduced or otherwise knocked down. Genes can be effectively edited using any of a variety of gene editing methods such as CRISPR/CAS9, zinc finger nuclease, or TALENs systems, and later-generation methods based on these technologies. Stop codons can be introduced into the ORF of the gene, or transcription response elements or promoters can be modified to attenuate transcription of the gene of interest. Genes, such as genes for expressing shRNA siRNA precursors can be "knocked-in" by gne editing methods. Thus expression of TERT can be attenuated, knocked down, or knocked out by genome editing methods. Although a number of methods exist for editing genomes, such as TALENs (transcription activator-like effector nucleases, see, e.g., Joung, J K, et al. "TALENs: a widely applicable technology for targeted genome editing" *Nat Rev Mol Cell Biol.* 2013 14(1): 49-55), the CRISPR/CAS9 system is currently at the forefront of gene editing methods. The clustered regularly interspaced short palindromic repeats (CRISPR)-CRISPR-associated protein 9 (Cas9) system is a bacterial defense mechanism against phage infection and plasmid transfer that has been repurposed as a potent RNA-guided DNA targeting platform for genome editing (see, e.g., Jiang, F., et al., "CRISPR-Cas9 Structures and Mechanisms" *Annu. Rev. Biophys.* 2017 46:505-29 for a detailed review of CRISPR/CAS9 function and methods, and Gundry, M. C. et al. Highly Efficient Genome Editing of Murine and Human Hematopoietic Progenitor Cells by CRISPR/Cas9. (2016) *Cell Rep* 17, 1453-1461).

Although genome modification by insertion of genes of interest and other genetic elements into chromosomes has significant potential, the transfer of the genetic material into a chromosome depends on the reliable and predictable function of the transgene without perturbing any endogenous gene and/or other regulation element. As such, random integration of a transgene presents a threat of unpredicted insertion or mutagenesis. The integration of the transgene into an acceptable site in the genome is preferable. One such site has been identified in connection with AAV viral integration. This site is known as AAVS1 (also known as the PPP1R2C locus) on human chromosome 19, which is a well-validated "safe harbor" to host a DNA fragment with expected function (see, e.g., Sadelain et al. "Safe Harbours for the Integration of New DNA in the Human Genome" *Nat Rev Cancer.* 2011 Dec. 1; 12(1):51-8). It has an open chromatin structure and is transcription-competent. Most importantly, there is no known adverse effect on the cell resulting from the inserted DNA fragment of interest. AAV vectors. A number of systems have been developed, including commercial systems, for "knocking in" genes into safe harbor sites, such as the CRISPR/CAS9 AAVS1 Safe Harbor Targeting Kit commercially available from System Bioscience, LLC, of Palo Alto, Calif., and the Human AAVS1 safe harbor gene knock-in kits and clones, commercially available from GeneCopoeia, Inc. of Rockville, Md.

Telomerase reverse transcriptase (TERT) is a ribonucleoprotein polymerase that maintains telomere ends by addition of the telomere repeat TTAGGG. Human TERT has two isoforms (see, e.g., Gene ID: 7015, Ensembl: ENSG00000164362, Uniprot: O14746, GenBank reference sequences include, for example: telomerase reverse transcriptase isoform 2: NM_001193376.1 (FIG. 1A) and NP_001180305.1, and telomerase reverse transcriptase isoform 1: NM_198253.2 (FIG. 1B) and NP_937983.2 (FIG. 1C)). Commercial human TERT-targeting siRNA reagents are available, for example, via ThermoFisher Scientific, targeting locations 1757, 1731, 1049, 1538, 285, 1532, 1739, 1781, among others, of NM_001193376.1, and viral vectors, such as lentiviral and AAV vectors, for expressing TERT siRNA, for example and without limitation, TERT AAV siRNA Pooled Vector, commercially available from Applied Biological Materials, of Richmond, BC, Canada. Further, the use of viral vectors, such as AAV vectors, is common, and one of ordinary skill can readily assemble siRNA-producing viral particles knowing the sequence of hTERT mRNA, and based on knowledge in the art.

In aspects, a device is provided comprising MSCs modified to decrease TERT expression or activity, as described herein, seeded onto a suitable cell growth scaffold that, in one aspect, is bioerodible, that is, it erodes in vivo over a time period ranging from weeks to about two years, at which time tissue is formed from the modified MSCs as described herein that replaces the scaffold as it degrades. The scaffold is a manufactured structure prepared from natural or synthetic polymer compositions and/or decellularized tissue (ECM). The scaffold may be in the form of a heart valve, a heart valve leaflet, a blood vessel, or any suitable shape. In one aspect, the scaffold comprises a biodegradable, polymeric heart valve tissue scaffold that generally comprises two portions, an annular portion and leaflet portions. The annular portion (forming a ring, but not necessarily defining any particular geometric shape such as a perfect circle or cylinder), is provided as a point of attachment of a polymeric heart valve scaffold when implanted in a patient, to tissue surrounding the device, such as the annulus of a heart valve (e.g., mitral, tricuspid, aortic, and pulmonary valves). For instance, when the device is placed in a heart, the annular portion is configured to abut against native heart valve tissue and/or surrounding tissue when implanted, and optionally provides a suturing and anchoring structure for attachment to the native tissue, as well as providing an aperture for blood flow through the valve structure. The second portion comprises two or more flexible, coaptating leaflets that are movable relative to the first, annular portion between an open configuration in which the leaflet permits blood flow through the aperture in a first direction, and a closed configuration in which the leaflet restricts blood flow through the aperture in a second direction, opposite the first direction. The leaflets may be joined with adjacent leaflets at a portion of their edges immediately adjacent to the support portion to form a commissure, and are not joined at a portion distal to the support portion, to permit blood to flow through the valve when it is open. When the valve is closed, the leaflets are concave, meaning that the concavity extends generally towards a central axis of the aperture of the annular portion, and the leaflets contact or coaptate with adjacent leaflets to form a seal. Unless indicated otherwise, in reference to the heart-valve structures described herein, concave means curved or extending towards the rotational, longitudinal, or central axis, and convex, means curved or extending outwards away from the rotational, longitudinal, or central axis. The terms coaptating, commissure, valve, and leaflet are in reference to, and generally may be configured to mimic similar structures in native heart valves, though the shapes, orientations, and sizes are adapted to provide a scaffolding for generation of nascent heart valve tissue from cells that infiltrate, and, over time, replace the biodegradable matrix of the valve structure. Chordae tendineae also can be considered to be part of the tricuspid valve and/or the mitral valve.

In another aspect, the scaffold comprises a biodegradable, polymeric heart valve tissue scaffold that generally comprises a heart valve leaflet to replace a damaged or otherwise insufficient heart valve leaflet.

A number of biocompatible, biodegradable elastomeric (co)polymers are known and have been established as useful in preparing cell growth scaffolds, for example, for use in preparation of the polymeric heart valve described below. Non-limiting examples of a synthetic bioerodible polymer useful in the devices described herein, include: a polyester, a polyester-containing copolymer, a polyanhydride, a polyanhydride-containing copolymer, a polyorthoester, and a polyorthoester-containing copolymer. In one aspect, the polyester or polyester-containing copolymer is a poly(lactic-co-glycolic) acid (PLGA) copolymer. In other aspects, the bioerodible polymer is selected from the group consisting of poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; and polyphosphazenes. Additional bioerodible, biocompatible polymers include: a poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones including polycaprolactone; or a polymer comprising monomers derived from carbonates including polycarbonate, polyglyconate, poly(glycolide-co-trimethylene carbonate), or poly(glycolide-co-trimethylene carbonate-co-dioxanone).

In aspects, diamines and diols are useful building blocks for preparing the (co)polymer compositions described herein. Diamines as described above have the structure $H_2N—R—NH_2$ where "R" is an aliphatic or aromatic hydrocarbon or a hydrocarbon comprising aromatic and aliphatic regions. The hydrocarbon may be linear or branched. Examples of useful diamines are putrescine (R=butylene) and cadaverine (R=pentylene). Useful diols include polycaprolactone (e.g., Mw 1000-5000), multi-block copolymers, such as polycaprolactone-PEG copolymers, including polycaprolactone-b-polyethylene glycol-b-polycaprolactone triblock copolymers of varying sizes. Other building blocks for useful diols include, without limitation glycolides (e.g., polyglycolic acid (PGA)), lactides, dioxanones, and trimethylene carbonates. Diisocyanates have the general structure OCN—R—NCO, where "R" is an aliphatic or aromatic hydrocarbon or a hydrocarbon comprising aromatic and aliphatic regions. The hydrocarbon may be linear or branched.

In a one aspect, the polymer composition comprises a biodegradable poly(ester urethane) urea (PEUU), poly(ether ester urethane)urea (PEEUU), poly(ester carbonate)urethane urea (PECUU), or poly(carbonate)urethane urea (PCUU). In some examples, the composition comprises poly(ester-urethane)urea (PEUU). PEUU can be synthesized using putrescine as a chain extender and a two-step solvent synthesis method. For example, a poly(ester urethane) urea elastomer (PEUU) may be made from polycaprolactonediol (MW 2,000) and 1,4-diisocyanatobutane, with a diamine, such as putrescine as the chain extender. A suitable PEUU polymer may be made by a two-step polymerization process whereby polycaprolactone diol (Mw 2,000), 1,4-diisocyanatobutane, and putrescine are combined in a 1:2:1 molar ratio though virually any molar feed ratio may suffice so long as the molar ratio of each monomer component is >0. In one aspect, the molar feed ratio of polycaprolactone diol plus putrescine is equal to that of diisocyanatobutane. A poly (ether ester urethane) urea elastomer (PEEUU) may be made by reacting polycaprolactone-b-polyethylene glycol-b-polycaprolactone triblock copolymers with 1,4-diisocyanatobutane and putrescine. In one aspect, PEEUU is obtained by a two-step reaction using a 2:1:1 reactant stoichiometry of 1,4-diisocyanatobutane:tri block copolymer: putrescine.

In another aspect, the composition comprises a poly(ester carbonate urethane)urea (PECUU) or a poly(carbonate)urethane urea (PCUU) material. PECUU and PCUU are described, for example, in Hong et al. (Tailoring the degradation kinetics of poly(ester carbonate urethane)urea thermoplastic elastomers for tissue engineering scaffolds Biomaterials, doi:10.1016/j.biomaterials.2010.02.005). PECUU is synthesized, for example, using a blended soft segment of polycaprolactone (PCL) and poly(1,6-hexamethylene carbonate) (PHC) and a hard segment of 1,4-diisocyanatobutane (BDI) with chain extension by putrescine. Different molar ratios of PCL and PHC can be used to achieve different physical characteristics. Putrescine is used as a chain extender by a two-step solvent synthesis method. In one example, the (PCL+PHC):BDI:putrescine molar ratio is defined as 1:2:1.

The cell growth scaffold also may comprise natural polymers, such as proteins, polysaccharides, glycosaminoglycans, etc., such as gellan gum, alginate, Kappa carrageenan, hyaluronic acid, or chondroitin sulfate. The natural polymer may be a single, isolated and purified ECM component, such as a purified collagen preparation, as are commercially available. An "ECM material," is a decellularized and/or devitalized material comprising or that is prepared from an extracellular matrix-containing tissue, and does not solely consist of a single, isolated and purified ECM component, such as a purified collagen preparation, as are commercially available. Any type of tissue-derived material can be used to produce the ECM materials in the methods, compositions and devices as described herein (see generally, U.S. Pat. Nos. 4,902,508; 4,956,178; 5,281,422; 5,352,463; 5,372,821; 5,554,389; 5,573,784; 5,645,860; 5,711,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666). The ECM material may be protease-solubilized, or otherwise-solubilized ECM material, such as ECM material that is acid-protease solubilized in acidic conditions—producing a reverse-gelling composition. In certain aspects, the ECM material is isolated from a vertebrate animal, for example and without limitation, from a mammal, including, but not limited to, human, monkey, pig, cow, and sheep. The ECM material can be prepared from any organ or tissue, including, without limitation, heart, urinary bladder, intestine, liver, esophagus, blood vessel, liver, nerve or brain, or dermis.

In various aspects, ECM material is decellularized, sterilized, and/or dried by any useful method. ECM-derived material can then be used in any form in the methods and compositions described herein. In certain aspects, in the context of depositing the ECM material to prepare the polymeric heart valve described herein, the ECM material is either finely comminuted, e.g., into micro-scale-sized (from 1-999 microns) or nano-scale-sized (from 1-999 nanometers) particles, or is solubilized, for example, in the form of solution, a pre-gel or gel, as described below.

The ECM material can be sterilized by any of a number of methods without loss of its ability to induce endogenous tissue growth. For example, the material can be sterilized by propylene oxide or ethylene oxide treatment, gamma irradiation treatment (0.05 to 4 mRad), gas plasma sterilization, peracetic acid sterilization, or electron beam treatment. Traditionally, ECM material is disinfected by immersion in 0.1% (v/v) peracetic acid ($\sigma$), 4% (v/v) ethanol, and 96% (v/v) sterile water for 2 h. The ECM material is then washed twice for 15 min with PBS (pH=7.4) and twice for 15 min with deionized water. International Patent Application Publication No. WO 2015/143310, the disclosure of which is incorporated herein by reference, describes further methods for sterilization of ECM materials.

Commercially-available ECM preparations can also be used in various aspects of the methods, devices and compositions described herein. In one aspect, the ECM is derived from small intestinal submucosa or SIS. Commercially available preparations include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). In another embodiment, the ECM is derived from dermis. Commercially available preparations include, but are not limited to, Pelvicol™ (crosslinked porcine dermal collagen, sold as Permacol™ in Europe; Bard Medical Division, Covington, Ga.), Repliform™ (Microvasive; Boston, Mass.), and Alloderm™ (LifeCell; Branchburg, N.J.). In another embodiment, the ECM is derived from urinary bladder. Commercially available preparations include, but are not limited to, UBM (Acell Corporation; Jessup, Md.).

A polymeric heart valve matrix described herein optionally comprises, in one aspect an extracellular matrix-derived gel (see, e.g., U.S. Pat. Nos. 8,361,503, and 8,691,276). In its broadest sense, ECM-derived scaffold materials are comminuted and solubilized to form a hydrogel. The solubilized hydrogel may or may not be dialyzed at any stage prior to solubilization, and in one aspect is not dialyzed prior to or after solubilization. Solubilization may be achieved by digestion with a suitable acid protease, such as chymotrypsin, pepsin, papain or elastase, under acidic conditions, such as between pH 1-4, or pH 1.5-2.5, e.g. pH 2.0, or in 0.01N HCl. In examples, the method for making such a gel comprises: (i) comminuting devitalized and/or decellularized tissue, (ii) solubilizing non-dialyzed or non-crosslinked devitalized and/or decellularized tissue by digestion with an acid protease in an acidic solution to produce a digest solution, (iii) raising the pH of the digest solution to a pH between 7.2 and 7.8 to produce a neutralized digest solution, and (iv) gelling the solution at a temperature greater than the gelation temperature (e.g., LCST) of the neutralized digest solution, typically greater than 25° C. or room temperature, thereby producing an ECM gel. In the context of the present invention, the neutralized digest solution (pre-gel, that is optionally lyophilized) is mixed with, co-deposited with, or deposited onto the polymer used to make the polymeric heart valve.

In one aspect of the solubilization of devitalized and/or decellularized tissue, the devitalized and/or decellularized tissue is solubilized with an acid protease. The acid protease may be, without limitation, pepsin. The material typically is solubilized at an acid pH suitable or optimal for the protease, such as greater than about pH 2, or between pH 1 and 4, or pH 1.5-2.5, for example, in a 0.01N HCl solution. The material typically is solubilized for 12-48 hours, depending upon the tissue type (e.g., see examples below), with mixing (stirring, agitation, admixing, blending, rotating, tilting, etc.) often on ice, at 4° C. or at room temperature (e.g., 20° C. to 23° C.). Once the material is solubilized, the pH is raised to between 7.2 and 7.8, and according to one embodiment, to pH 7.4. Bases, such as bases containing hydroxyl ions, including NaOH, can be used to raise the pH of the solution. Likewise buffers, such as an isotonic buffer, including, without limitation, Phosphate Buffered Saline (PBS), can be used to bring the solution to a target pH, or to aid in maintaining the pH and ionic strength of the gel to target levels, such as physiological pH and ionic conditions. The neutralized digest solution can be gelled at temperatures approaching 37° C., typically at any temperature over 25° C., though gelation proceeds much more rapidly at temperatures over 30° C., and as the temperature approaches physiological temperature. The method, according to one aspect, does not include a dialysis step prior to gelation, yielding a more-complete ECM-like matrix that typically gels at 37° C. more slowly than comparable collagen or dialyzed ECM preparations.

In certain aspects, the polymeric matrix of the heart valve comprises one or more therapeutic agents. For example, at least one therapeutic agent is added to the polymer composition described herein before it is implanted in the patient or otherwise administered to the patient. Generally, the therapeutic agents include any substance that can be coated on, embedded into, absorbed into, adsorbed to, or otherwise attached to or incorporated onto or into the polymeric heart valve described herein. Non-limiting examples of such therapeutic agents include: growth factors, chemoattractants, cytokines, antimicrobial agents, emollients, retinoids, and steroids. Each therapeutic agent may be used alone or in combination with other therapeutic agents.

In some examples, the polymer composition further comprises, for example and without limitation, a biomacromolecular component derived from ECM. In one example, the polymer composition comprises the biomacromolecule collagen so that collagenase, which is present in situ, can degrade the collagen. As an example, the polymer composition may comprise one or both of a collagen and an elastin. Collagen is a common ECM component, and typically is degraded in vivo at a rate faster than many synthetic bioerodible polymers. Therefore, manipulation of collagen content in the polymer composition may be used as a method of modifying bioerosion rates in vivo. Collagen may be present in the polymer composition in any useful range, including, without limitation, from about 2% wt. to about 95% wt., from about 25% wt. to about 75% wt., inclusive of all ranges and points therebetween, including from about 40% wt. to about 75% wt., including about 75% wt. and about 42.3% wt. Elastin may be incorporated into the polymer composition in order to provide increased elasticity. Elastin may be present in the polymer composition in any useful range, including without limitation, from about 2% wt. to about 50% wt., inclusive of all ranges and points therebetween, including from about 40% wt. and about 42.3% wt., inclusive of all integers and all points therebetween and equivalents thereof. In one non-limiting example, collagen and elastin are present in approximately equal amounts in the polymer composition. In another embodiment, the sum of the collagen and elastin content in the polymer composition is in any useful range, including, without limitation, from about 2% wt. to about 95% wt., and preferably in the range of from about 25% wt. to about 75% wt., inclusive of all ranges and points therebetween, including from about 40% wt. to about 75% wt., including about 75% wt. and about 42.3% wt.

Cell growth matrices can be formed by any useful method, for example, by solvent casting in a mold, for example, with particulate leaching to produce a porous structure, by 3D printing, dry spinning methods, or by electrodeposition. In one aspect, the structure is cut from a polymeric mesh comprising synthetic and/or natural (e.g., ECM) polymer compositions. In one aspect, for illustrative purposes, a polymeric mesh is electrodeposited, e.g., electrospun onto a target, such as a mandrel, and the resultant structure is shaped, e.g., by cutting, into shapes such as heart valve leaflet shapes or annular shaped (see, for example, U.S. Pat. Nos. 8,535,719 B2 and 9,237,945 B2, and United States Patent Application Publication No. 2014/0377213 A1, each of which is incorporated herein by reference in its entirety for their disclosure of electrospinning methods, and variations on electrospun matrices, including synthetic and natural components). While the polymeric mesh may be isotropic, the nature of heart valve leaflet and annulus ECM often is, in part, anisotropic, and as such, the polymeric matrix that is used to prepare the heart valve may be deposited in an oriented manner, and is therefore anisotropic. Electrospinning and electrodeposition methods are broadly-known, and in electrodeposition, relative movement of the nozzles/spinnerets and target surface, e.g., by deposition onto a rotating mandrel, during electrodeposition can be used to produce an oriented pattern of fibers. As is further broadly-known, more than one polymer composition can be electrodeposited concurrently, or in a desired order, to create a layered structure. Further, solutions comprising other polymers, ECM materials (e.g., ECM gel, or solubilized ECM), cell-culture medium, cells, such as stem cells including the modified MSCs or ASCs described herein, blood products, therapeutic agents, and the PCL ECM soluble fraction as described herein, can be electrosprayed onto, or into the formed fiber structure, with variable deposition timing to create optimal layering.

The properties of electrospun elastomeric matrices can be tailored by varying the electrospinning conditions. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice. In certain embodiments, the biased target is moved back and forth in a regular, periodic fashion, such that fibers of the non-woven mesh are substantially parallel to each other. When this is the case, the resulting non-woven mesh may have a higher resistance to strain in the direction parallel to the fibers, compared to the direction perpendicular to the fibers. In other embodiments, the biased target is moved randomly relative to the orifice, so that the resistance to strain in the plane of the non-woven mesh is isotropic. The target can also be a rotating mandrel. In this case, the properties of the non-woven mesh may be changed by varying the speed of rotation. The properties of the electrospun elastomeric scaffold may also be varied by changing the magnitude of the voltages applied to the electrospinning system.

Electrospinning may be performed using two or more nozzles, wherein each nozzle is a source of a different polymer solution. The nozzles may be biased with different biases or the same bias in order to tailor the physical and chemical properties of the resulting non-woven polymeric mesh. Additionally, many different targets may be used. In addition to a flat, plate-like target, a mandrel may be used as a target. When the electrospinning is to be performed using a polymer suspension, the concentration of the polymeric component in the suspension can also be varied to modify the physical properties of the elastomeric scaffold. For example, when the polymeric component is present at relatively low concentration, the resulting fibers of the electrospun non-woven mesh have a smaller diameter than when the polymeric component is present at relatively high concentration. One skilled in the art can adjust polymer concentrations to obtain fibers of desired characteristics. Useful ranges of concentrations for the polymer component include from about 1% wt. to about 15% wt., from about 4% wt. to about 10% wt., and from about 6% wt. to about 8% wt.

In electrospinning, polymer fibers are often deposited about the circumference of a mandrel and to generate a planar or substantially planar structure, the electrodeposited mat/matrix is cut substantially in the direction of the rotational axis of the mandrel, or in any manner to generate a useful topology, such as the shape of a heart valve, a heart valve leaflet, or portion thereof. In use, more than one electrospun mats/matrices can be attached by any useful means, such as by "sewing" using sutures, heat annealing, chemical annealing/cross-linking, etc., though it should be recognized that the method of attaching the two or more mats/matrices would have to be strong enough for the end use, e.g., to resist breakage, rupture, or herniation.

Although any form of spraying is expected to be effective, liquid, e.g., cell growth media, ECM pre-gel, cells, a blood product, such as serum, plasma, or platelet-rich plasma, or a therapeutic composition may be electrosprayed. Electrospraying can be done before, after, or concurrently (intermittently or continuously) with the electrodeposition of polymer fibers, and is conducted in an essentially identical manner. The composition and structures according to any aspect described herein can also include an active agent, such as, without limitation, one or more of an antiseptic, an antibiotic, an analgesic, an anesthetic, a chemotherapeutic agent, an anti-inflammatory agent, a metabolite, a cytokine, a chemoattractant, a hormone, a steroid, a protein, or a nucleic acid, e.g., as are broadly-known.

Cells, e.g., a patient's (autologous) cells or allogeneic cells, may be pre-deposited onto the matrix, and cultured ex vivo in a suitable bioreactor or culture vessel, as are known in the cell and tissue culture fields. A patient's stem cells (e.g., modified MSCs, as described herein), progenitor cells, blood, or blood cells may be deposited (seeded) onto the matrix. Alternatively, or in conjunction with the ex vivo culturing, the device is implanted, and by virtue of contact with circulating blood cells and adjacent tissue, such as valve annulus tissue, the polymeric heart valve is infiltrated with and populated by the patient's cells. Heart valve leaflets have been generated in vivo in animals using single polymeric (PEUU, PCUU or PECUU) heart valve leaflet matrices sewn into heart valves.

According to one aspect of the invention, a method of preparing a cardiovascular graft is provided. The method comprises seeding a bioerodible cell growth scaffold with mesenchymal stem cells (MSCs) that are modified to reduce or eliminate expression or activity of telomerase reverse transcriptase (TERT). As used herein, a cell may be "modified" in any fashion to reduce or eliminate TERT expression or activity, such as TERT osteogenic-inducing activity. In one aspect, the cell is genetically-modified to express a gene that expresses a functional RNA, such as, without limitation, a shRNA for production of an interfering RNA, or a ribozyme, or expresses a protein that interferes with non-canonical TERT activity (transcript regulatory activity, and not telomere-extending activity), such as, without limitation: a binding reagent that binds TERT, such as an scFv fragment; a decoy for TERT; or an antagonist that interferes with activity of TERT, such as the osteogenic-inducing activity of TERT. In another sense, the cells may be modified, e.g., by gene editing, to reduce expression of TERT, either as a knockout, by shutting off expression of TERT at any level, for example, at the transcription level by modifying the promoter region of the TERT gene, or at the translation level, for example, by introducing a stop codon into the TERT ORF. Transient expression systems, such as a recombinant AAV genome expressing a shRNA for TERT silencing by RNAi, may be used to some effect, but would need multiple treatments. Antisense RNA or other antisense reagents, or other transiently-effective therapeutics having the ability to decrease expression or activity of TERT, may be used during seeding and can be continued afterwards, but are not necessarily an ideal, permanent treatment modality, unless gene transfer or editing is prohibited. In aspects, the MSCs, e.g., human or autologous MSCs or ADSCs, are genetically-modified, for example and without limitation, by inserting a gene for expressing a shRNA that is processed to produce siRNA for silencing or knocking down TERT expression. The gene is optionally delivered to a safe-harbor site in the genome of the MSCs, such as the AAVS1 site, using gene editing methods, e.g., as described herein.

In the method, the modified MSCs are seeded onto a suitable cell growth scaffold, such as a bioerodible scaffold comprising a polyester, polyurethane, polycarbonate, polyether, PEUU, PEEUU, PECUU, or PCUU polymer composition. The cell growth scaffold may be formed into the shape and size of a heart valve, a heart valve annulus, a heart valve leaflet, or a blood vessel. The modified MSCs can then be cultured in vitro (ex vivo) to permit infiltration of the cells onto and/or into the matrix of the cell growth scaffold, and optionally for a length of time to allow for expansion of the population of the MSCs and cells differentiated therefrom, including valve interstitial cells (valvular interstitial cells, or VICs), and endothelial cells (ECs), such as valve endothelial cells (valvular endothelial cells) or vascular endothelial cells, and lineage intermediates between the MSCs and the VICs or ECs. The seeded scaffold can be cultured in any suitable tissue culture vessel, in any suitable medium for propagation of MSCs or ECs, including differentiation media, as is necessary to drive the MSCs to the appropriate lineage. Culture media for such purposes are broadly-known, and are commercially available, as suitable tissue culture vessels, such as plates, flasks, and bioreactors.

Once the MSCs are permitted to infiltrate the cell growth scaffold, and optionally to propagate and/or differentiate on and in the scaffold for an appropriate length of time, the resulting tissue construct can be implanted into a patient at an appropriate site for integration with the patient's tissue. The tissue construct can be sutured, stapled, or glued, for example and without limitation, using fibrin or cyanoacrylate glue, into place as is well understood in the field of the invention.

Thus, in another aspect, a method of treating a cardiovascular defect or injury in a patient is provided. The method comprises implanting or depositing at a site of a defect or injury in a patient, a cell growth scaffold or matrix with mesenchymal stem cells (MSCs) that are modified to reduce or eliminate expression or activity of telomerase reverse transcriptase (TERT). The defect or injury can be a congenital defect or malformation, such as a valve defect or stenosis, or a damaged valve as a result of disease, traumatic injury, age (e.g., calcification), or any other etiology. Likewise, a damaged, stenotic, or otherwise defective blood vessel may be repaired or replaced using a tubular, modified MSC-seeded cell growth scaffold, as described herein. A defective or damaged blood vessel can be excised, and a seeded scaffold anastamosed in-line with native vasculature. According to a further aspect of the invention, a prosthetic cardiovascular graft is provided. By "prosthetic, it is meant a man-made replacement for an original anatomical feature, such as a heart valve or a heart valve leaflet. The graft comprises mesenchymal stem cells (MSCs) that are modified to reduce or eliminate expression or activity of telomerase reverse transcriptase (TERT) or cells differentiated from the modified MSCs, such as VICs or ECs. The cardiovascular graft may be formed into any useful shape, such as, without limitation, prosthetic heart valves and prosthetic heart valve leaflets (see, FIGS. 2 and 3A-3E) prosthetic blood vessels (see, FIG. 4). The cells are optionally integrated into a cell growth scaffold, such as a bioerodible cell growth scaffold, which means that the MSCs that are modified to reduce or eliminate expression or activity of telomerase reverse transcriptase (TERT) or cells differentiated from the modified MSCs, such as VICs or ECs, are attached to a surface of the scaffold, or dispersed uniformly or non-uniformly, into the scaffold, e.g., mixed with the composition used to form the scaffold, or deposited or migrated into interstices or pores within the scaffold that are present either upon formation of the scaffold, or as a result of incomplete bioerosion of the scaffold. Depending on culture conditions, culture media, and the length of time the structure is cultured ex vivo, the scaffold might comprise predominantly modified MSCs, or may comprise cell populations differentiated from the modified MSCs, such as VICs or ECs.

International Patent Publication No. WO 2016/138416, incorporated herein by reference, depicts exemplary heart valve cell growth scaffolds and an exemplary method of making prosthetic heart valve prosthetics by electrospinning. An exemplary prosthetic tricuspid valve device 210 is shown in FIG. 2. The valve 210 comprises a support portion 220 defining a longitudinal axis 222 and an aperture 225 passing through the valve 210; and three concave leaflets 230 extending longitudinally from a distal end 234 of the support portion 220, wherein each leaflet 230 comprises a concave belly or central region 235 and a commissure 236 joining adjacent leaflets 230. The fiber matrix at the central region 235 and commissures 236 is anisotropic, with different fiber orientations at the central region 235 and commissures 236, with the fiber orientation at the central region 235 being more circumferential than at the commissures 236.

An exemplary prosthetic bicuspid valve device 340 is shown in FIGS. 3A-3E. The valve 340 is formed from a matrix of fibers and comprises a support portion 341 defining a longitudinal axis 342 and an aperture; and two concave leaflets 343 extending longitudinally from the support portion 341, wherein each leaflet portion comprises a central region 335 and commissures 346, joining the leaflets. FIGS. 3B and 3D provide a top view of the bicuspid valve 340 along the longitudinal axis in a closed and open position, respectively. FIGS. 3C and 3E depict the valve 340 along X in corresponding FIGS. 3B and 3D. FIGS. 3B and 3C depict the valve 340 in a closed configuration, and FIGS. 3D and 3E depict the valve in an open configuration where blood flows in the direction of the arrow. Note that the bicuspid valve leaflets have a radially-curved profile, with one leaflet larger than the other.

In any aspect of the valve structures described herein, the identification of a cylindrical portion is merely illustrative and exemplary of one possible geometry of potential support structures (e.g., support portions) for the leaflets. In practice, and in alternate embodiments, the support structure can take on any useful shape, so long as it can support the leaflet function, and anchor the valve in place, for example, by serving at least in part as a sewing ring, or providing an attached sewing ring, for suturing the structure in place during implantation, and/or for attachment to additional support or placement structures. Cylindrical shape may be considered the simplest, and most appropriate geometry for purposes herein. The leaflet portions of the valves depicted in FIGS. 2 and 3A-3E are flexible and concave, and, when in a closed configuration or position, are in contact with (coaptate) adjacent leaflets distal to the cylindrical or support portion of the prosthetic valve to prevent blood backflow. When in an open configuration, the leaflets extend the aperture of the (e.g., cylindrical) support structure, permitting blood flow through the device. Of note is that for any valve structure, the leaflets do not have to be symmetrical in size, as with native mitral and tricuspid valves. In any instance, the shape of the leaflet can be referred to as a "leaflet shape," such as a mitral, tricuspid, aortic, or pulmonary valve leaflet-shape, or a pathological mitral, tricuspid, aortic, or pulmonary valve leaflet-shape, referring to native or damaged/pathological shapes of leaflets or cusps of valves of an organism, such as a human, or a mammal.

Figure 4:
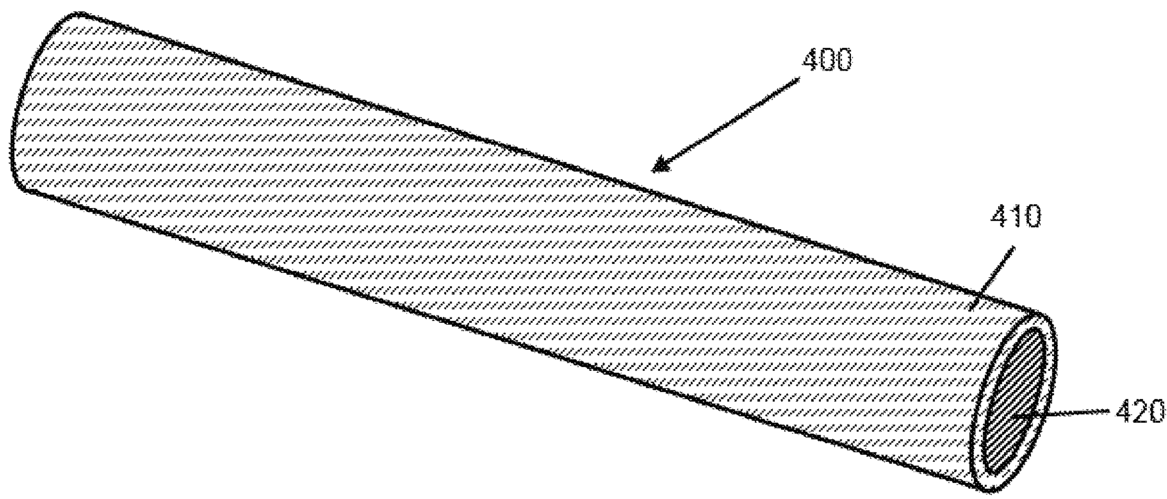
FIG. 4 depicts schematically a prosthetic blood vessel.

FIG. 4 depicts schematically a tube-shaped, prosthetic blood vessel device 400 having a wall 410 of a suitable bioerodible cell growth scaffold material, seeded with modified MSCs according to any aspect described herein, and/or cells derived therefrom, such as vascular endothelial cells, and the wall defining a lumen 420.

In use, the bioerodible cell growth scaffold material in the shape of a heart valve, a heart valve leaflet, a blood vessel, or any suitable shape, is seeded with the modified MSCs and is typically placed in culture long enough for the MSCs to attach to a surface of the device, and/or to infiltrate into pores or interstices of the wall. The device can then be implanted into a patient's heart or vasculature immediately, or after culturing for a length of time suitable to establish cell propagation and optionally differentiation on and/or within the scaffold.

Example 1

Calcific aortic valve disease (CAVD) is present in ~2% of individuals over 60 years of age. Senescence is a proliferative control mechanism usually associated with aging whereby different factors such as telomere shortening, DNA damage, and chromatin acetylation or methylation, limit cellular proliferation. The objective of this study is to evaluate the different roles of TERT in CAVD.

Figure 5:
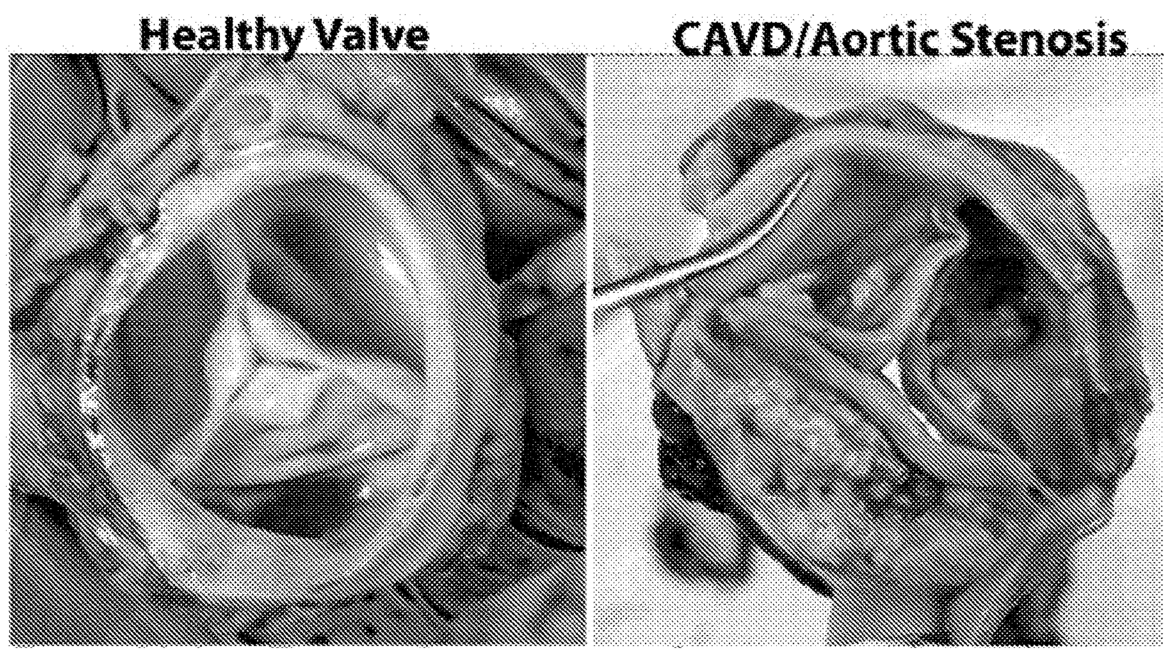
FIG. 5 provides photographs of representative heart valves from a healthy control patient (left), and a patient with severe CAVD and aortic stenosis (right).

FIG. 5 shows representative heart valves from a healthy patient, and a patient with severe CAVD and aortic stenosis. As can be seen in FIG. 5, the calcified valve leaflets cannot properly close. Different staining techniques were used to categorize human valves into calcified and healthy. Immunofluorescent staining was used to identify the presence and localization of TERT the tissues. Valve interstitial cells (VICs) from the same donors and MSC were cultured under osteogenic conditions and the calcification and the expression of TERT were assessed. RNA expression of TERT and other gene of interest were studied by qPCR. TERT activity was inhibited by BIBR1532,

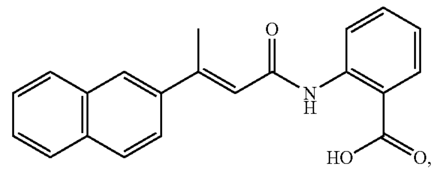 [SMILES: C/C(=C\C(=O)Nc1ccccc1C(=O)O)c1ccc2ccccc2c1]

in MSC and these cells exposed to osteogenic media, assessing calcification. Calcification was also studied in VSMC from Wild Type and TERT-KO mice aorta exposed to ostegenic media.

TERT, Runx2, OSTERIX and alpha-actin appeared increased and Notch1 and BAF57 reduced in calcified valves compared to control. Similar results were obtained using VICs and MSC exposed to osteogenic media. The calcium staining and posterior quantification showed a higher predisposition of cells from CAVD valves to calcify compared to those from healthy controls. Blocking TERT activity reduced calcification in MSC. Knocking down TERT expression reduced expression of osteogenic genes. VSMCs from KO-TERT mice did not calcify whilst the Wild Type VSMC did. These results indicate that TERT is positively associated with the calcification process.

Figure 6:
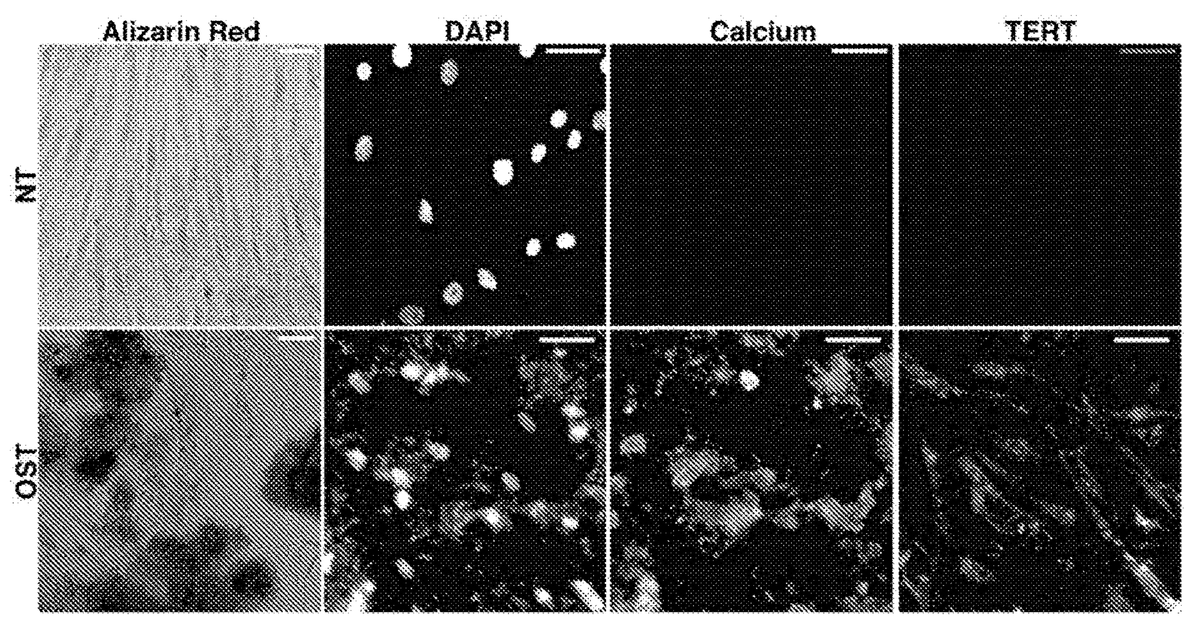
FIG. 6 provides photomicrographs (originals in color) showing that after 14 days in osteogenic medium, hMSCs have begun to differentiate down the osteoblast lineage as detected by Alizarin red stain (left panels). At this time, they also exhibit a significant increase in TERT protein (middle panel, red in original) in both the cytoplasm and nucleus of cells near calcified nodules (stained with OsteoImage™ green). Scale bar, 50 μm.

To establish that endogenous TERT was expressed during osteogenesis, we cultured hMSCs under osteogenic conditions (a defined medium supplemented with β-glycerolphosphate, ascorbate, and dexamethasone; henceforth called osteogenic conditions, osteogenic media, or osteogenic assay). In the osteogenic assay, cells are grown until confluence, and then osteogenic media is added, thus cells have low levels of proliferation for the duration of the osteogenic assay. hMSCs were treated under osteogenic conditions for 14 days, a point at which hMSCs are beginning to lay down calcified matrix, and we found increased levels of TERT protein in calcifying cells (FIG. 6), indicating a role for endogenous TERT in osteogenesis. Staining shows increased levels of TERT in both cytoplasmic and nuclear locations, suggestive of non-canonical, non-telomere extending activities of TERT.

Figure 7:
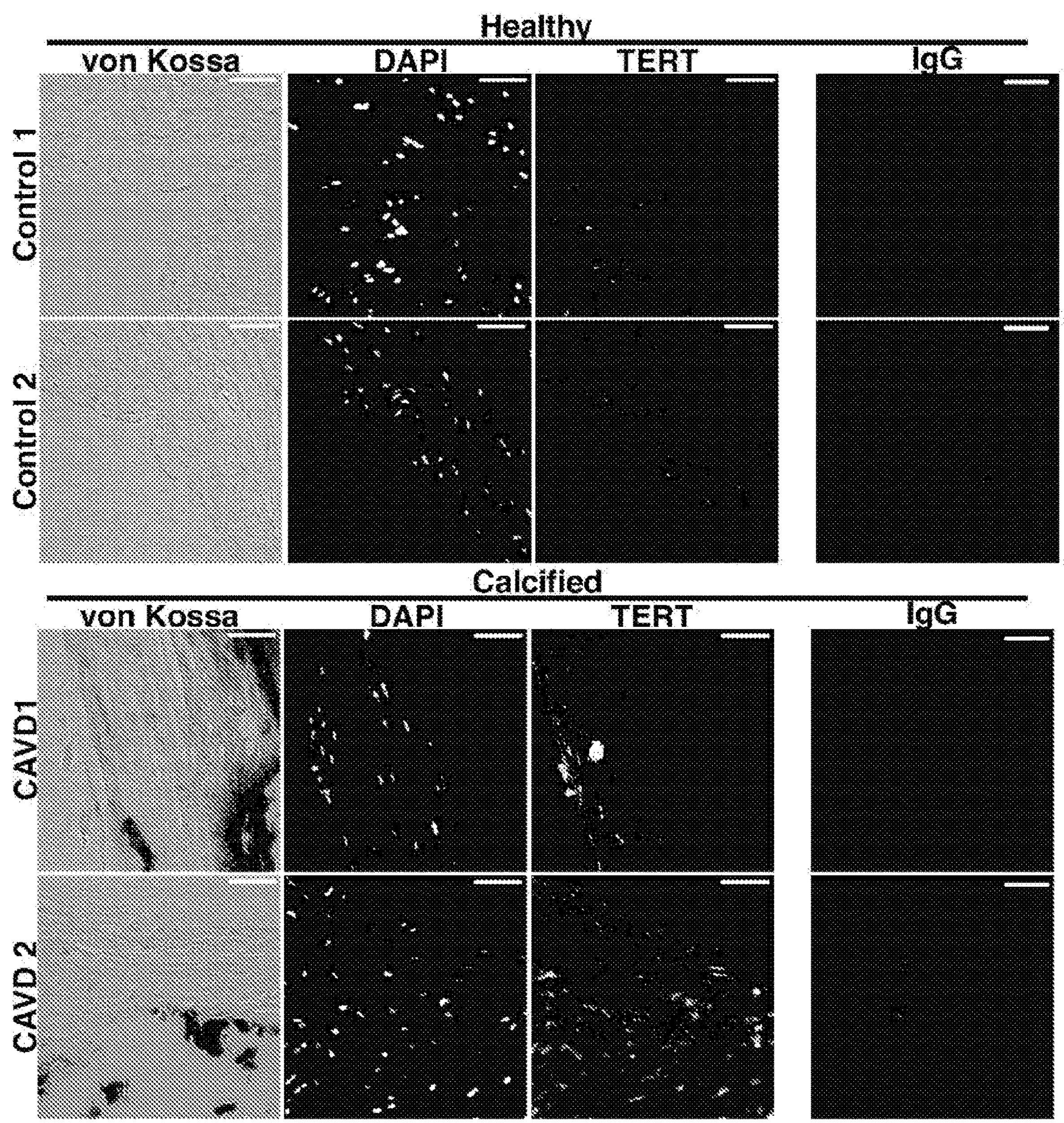
FIG. 7 provides photomicrographs showing that TERT is upregulated in CAVD valve tissues. Scale bar, 50 um.

To establish if TERT protein is present in valve calcification, we performed immunohistological analysis on valve tissues isolated from non-CAVD controls (henceforth the terms non-CAVD controls and healthy controls are used interchangeably) or patients with CAVD and found very little to no TERT-positive staining in healthy valve tissues, while CAVD valves stained positive for TERT near areas of calcification (FIG. 7). Von Kossa stain was used to detect the presence of calcification (dark precipitation), and on adjacent slides immunohistochemistry was performed to detect for the presence of TERT protein. TERT was significantly upregulated in both the cytoplasm and nuclei in valves from patients with CAVD, and low to undetectable in controls. Representative images, n=5 tissues each group.

Figure 8A:
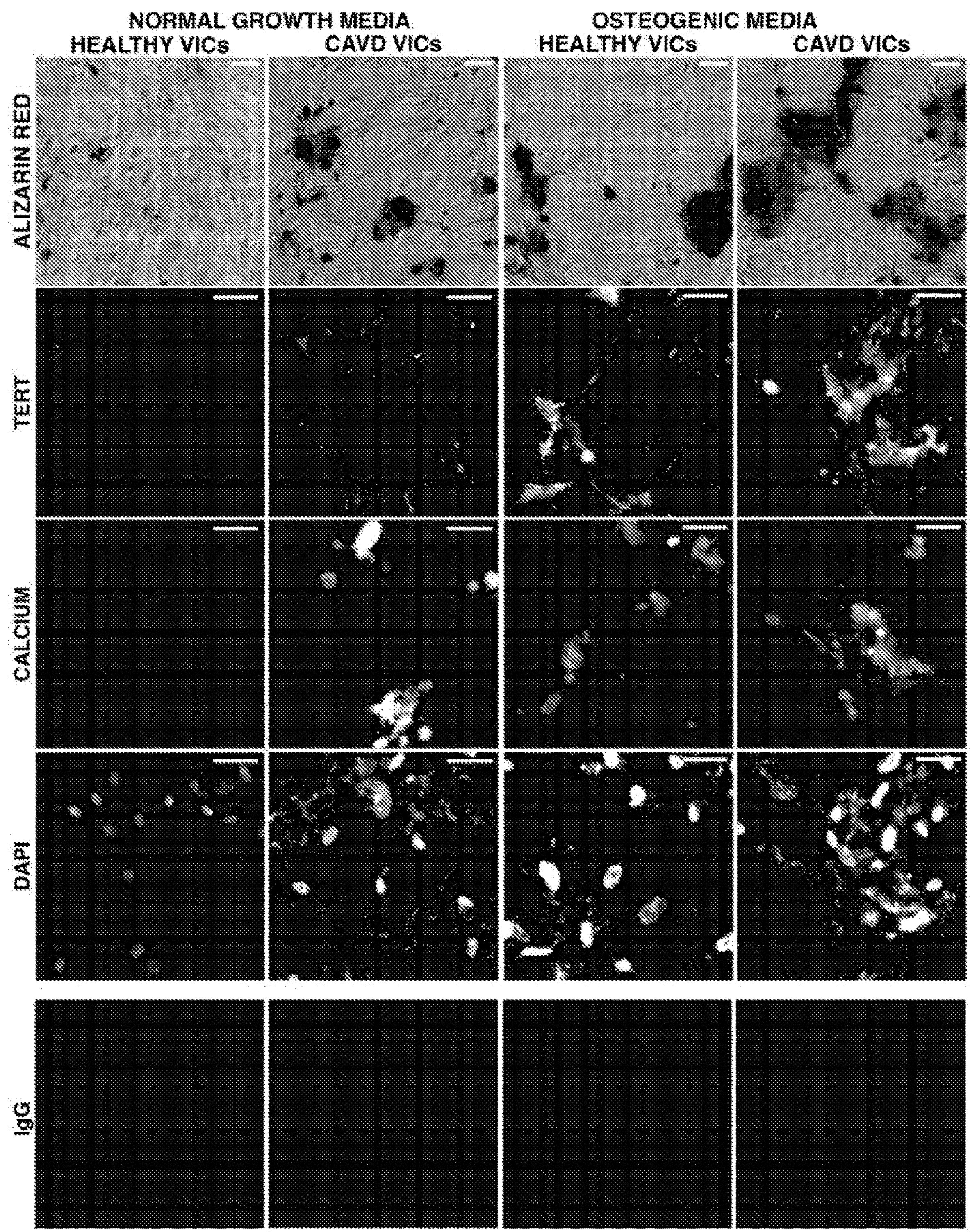
FIGS. 8A-8C provide photomicrographs, a photograph, and a graph, respectively, showing that calcifying VICs exhibit increased TERT protein levels. Scale bar, 50 um.
Figure 8B:
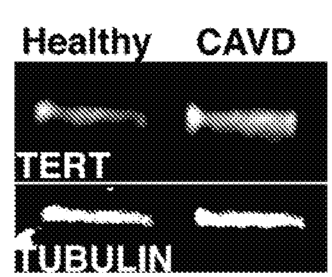
Figure 8C:
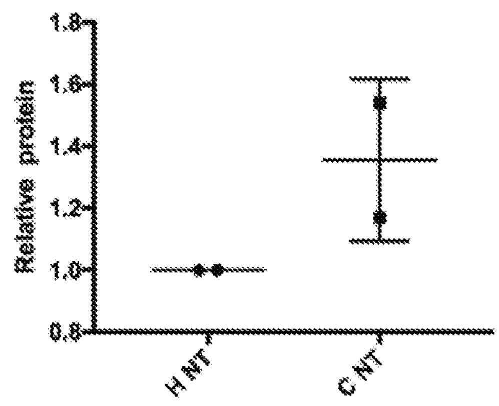

Calcification is often localized to the collagen-rich fibrosa layer, which is heavily populated with valve interstitial cells (VICs). We currently have isolated 29 primary VIC cell lines, including 22 non-CAVD control and 7 from CAVD valves in our valve tissue biorepository. Under basal conditions CAVD VICs spontaneously calcify, and similar to in vivo tissue staining, VICs from non-CAVD control valves show no TERT staining, while VICs from CAVD valves exhibit TERT-positive cells near calcified nodules (FIG. 8A, left panels). After 14 days of treatment with osteogenic differentiation medium, non-CAVD control VICs develop calcification and increase the amount of TERT protein (FIG. 8A, right panels). Western blot analysis confirms the upregulation of TERT protein in CAVD VICs compared to healthy VICs (FIG. 8B). These data suggest TERT is upregulated during the phenotypic switch from a non-calcifying to a calcifying VIC.

Figure 9:
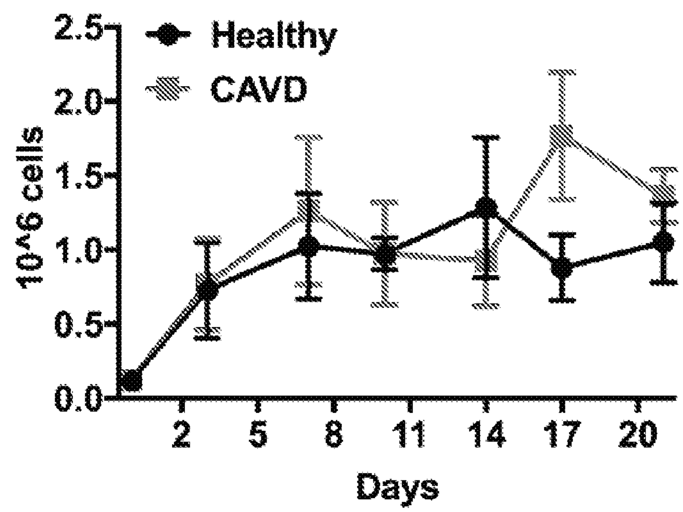
FIG. 9 provides a graph showing no changes in proliferation rates between healthy and CAVDs VICs.

TERT is best known for its telomere-extending functions, thus with higher levels of TERT protein it was important to assess proliferation rates and telomere length in our VIC lines. There is no change in the proliferation rate of healthy or CAVD VIC lines throughout the 21-day osteogenic assay (FIG. 9). VICs were isolated from healthy and CAVD valves by, in short, collagenase II digestion. The VICs were plated at $0.12 \times 10^6$ cells per well and cell number was quantified every three days for 3 weeks. n=3 biological replicates from cell lines isolated from 3 individuals for each group; each cell line was run in quintuple. No statistical difference was observed in the proliferation rate of healthy or CAVD VICs (FIG. 9).

Figure 10:
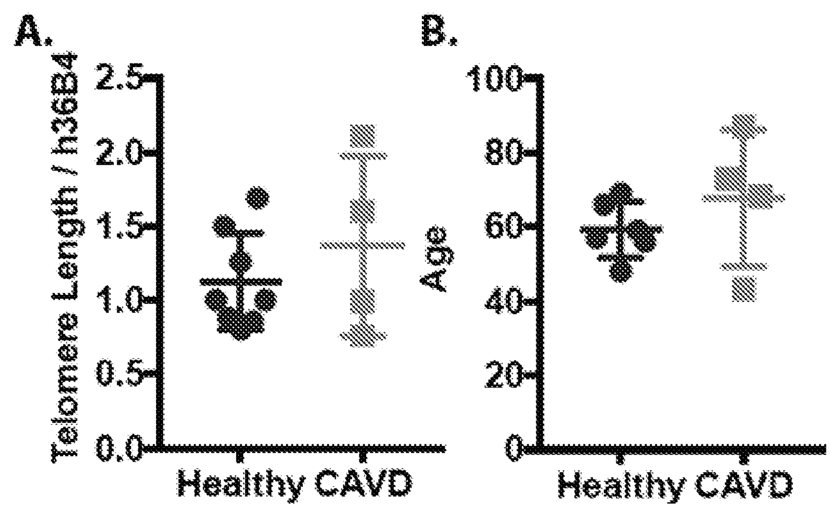
Figure 11:
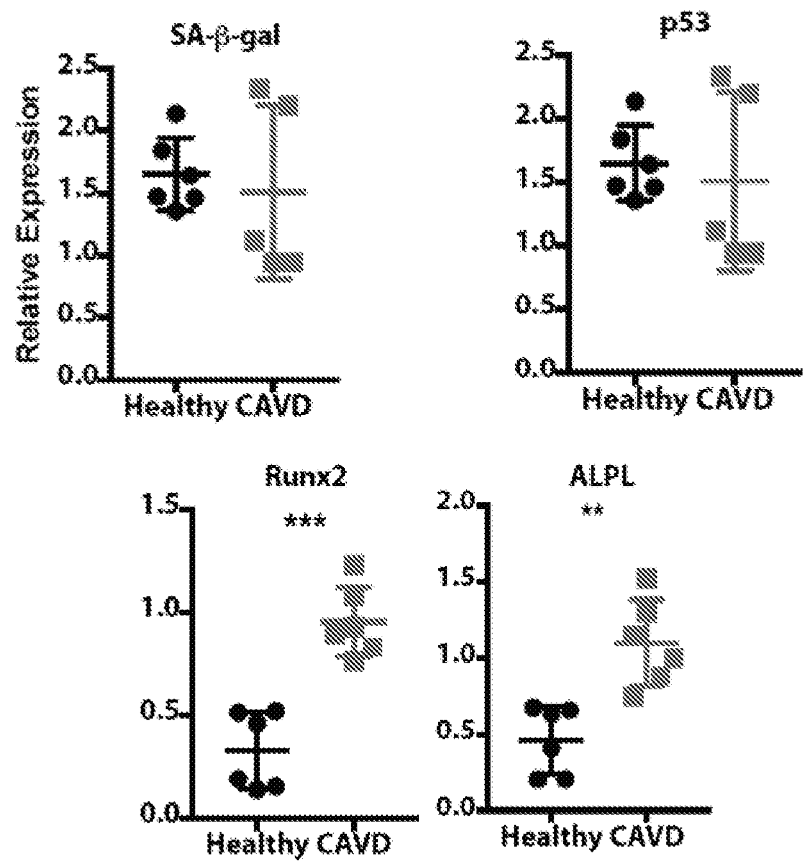
FIG. 11 provides graphs showing upregulation of osteogenic genes, but not senescence-associated genes, in CAVD VICs at baseline.

Genomic (g) DNA was isolated from healthy and CAVD VICs. Primary VICs were isolated from tissues and expanded for two passages and then frozen. Frozen vials of cells were used to isolate gDNA. Telomere length was normalized to the 36B4 house keeping gene. n=8 Control, 4 CAVD biological replicates, each run in triplicate. Telomere length was analyzed by real-time quantitative (q) PCR analysis. The mean age of healthy and CAVD patients in our biorepository is 59 and 67 years old, respectively. No significant difference in telomere length (FIG. 10 (A)), or age (FIG. 10 (B)), was observed between healthy and CAVD VICs. n=6 biological replicates each group, run in triplicate. Statistical analysis was performed using unpaired two-tailed student's t-test and showed not significant differences. Gene expression analysis of cells at basal conditions showed that senescence-associated β-galactosidase (SA-β-gal) did not differ between healthy and CAVD groups (FIG. 11). Together, these data indicate that the upregulation of TERT does not generate differences in telomere length between healthy and CAVD VICs.

FIG. 11 shows upregulation of osteogenic genes (Runx2 and tissue non-specific alkaline phosphatase (ALPL)), but not senescence-associated genes (SA-β-gal, in CAVD VICs at baseline). RT-qPCR analysis was used to quantify expression. Cells were cultured under normal growth conditions and mRNA was isolated when cells reached confluence. Data shows expression is shown relative to **18*s* RNA. n=6 biological replicates each group, run in triplicate. Statistical analysis was performed using unpaired two-tailed student's t-test and showed not significant differences. $^{}p<0.01$ $^{***}p<0.001$ two-tailed student's t-test.

Figure 12:
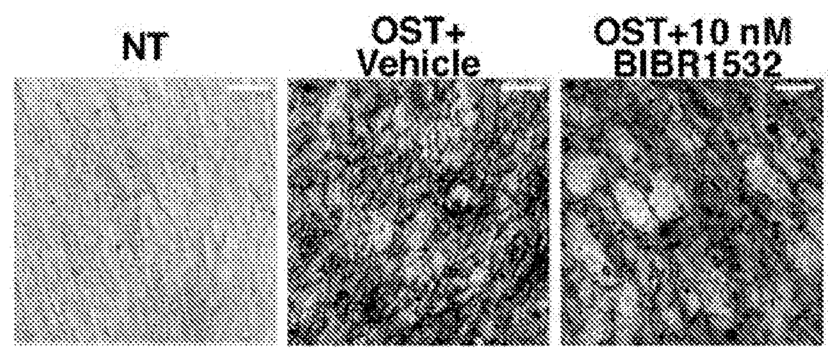
FIG. 12 provides photomicrographs showing that inhibition of TERT's telomere-extending enzymatic activity does not affect calcification. Scale bar, 10 um.

Human mesenchymal stem cells were cultured in osteogenic media with vehicle (DMSO) or the TERT inhibitor BIBR 1532. Cells were treated every other day for 14 days. At day 14 cells were fixed in 4% paraformaldehyde, washed with water, then stained with 40 mM Alizarin Red S, pH 4.1-4.3 for 20 minutes with shaking. Cells are then washed with water and imaged. This data (FIG. 12) suggests that TERT participates in the calcification process, but not in a canonical way.

Figure 13:
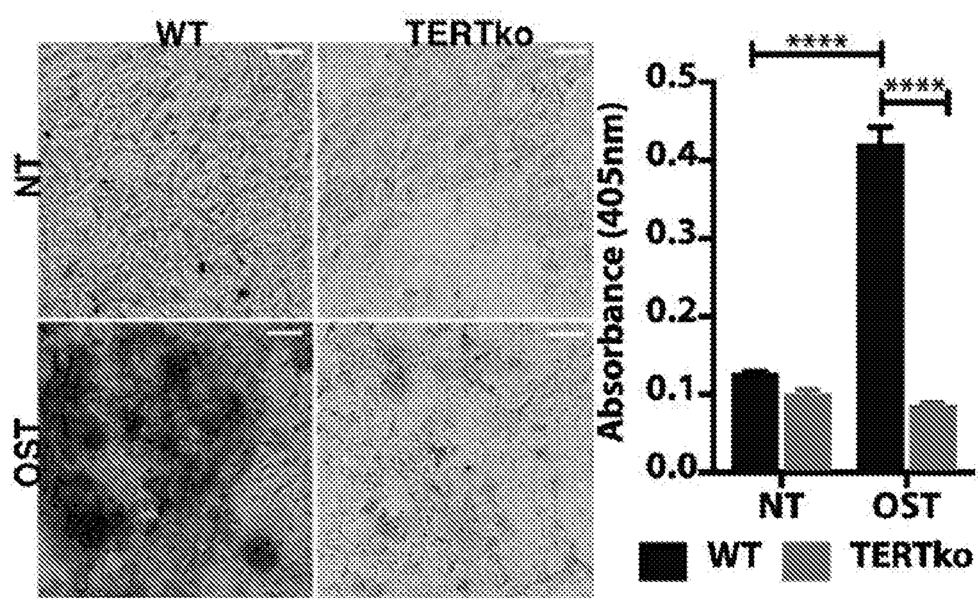
FIG. 13 provides photomicrographs and a graph, respectively, indicating that genetic deletion of TERT prevents calcification. Scale bar, 50 um.

To establish a role for TERT in the phenotypic switch from a healthy to a calcified cell, we utilized VSMCs isolated from wildtype (WT) and TERT knockout (TERTko) mice. While WT VSMCs exhibited robust calcification after 21 to 28 days of osteogenic treatment, TERTko VSMCs did not calcify (FIG. 13). Aortic vascular smooth muscle cells (VSMCs) were obtained from wild type (WT) mice and from TERT knockout (TERTko) mice. Cells were incubated for 21-28 days in osteogenic media. Alizarin red staining was used to show that while VSMCs isolated from WT mice were seen to calcify, VSMCs from TERTko mice did not calcify (FIG. 13, left). The graph provided in FIG. 13, right, quantifies the data shown in the photomicrographs, showing Alizarin red absorbance at 405 nm. $^{****}p<0.0001$ two-way ANOVA, n=3 each group.

Together, these data demonstrate that TERT is necessary for the osteogenic switch in these cells, and these effects are not due to TERT's telomere-extending activity, suggesting a non-canonical role in the calcification process.

Figure 14A:
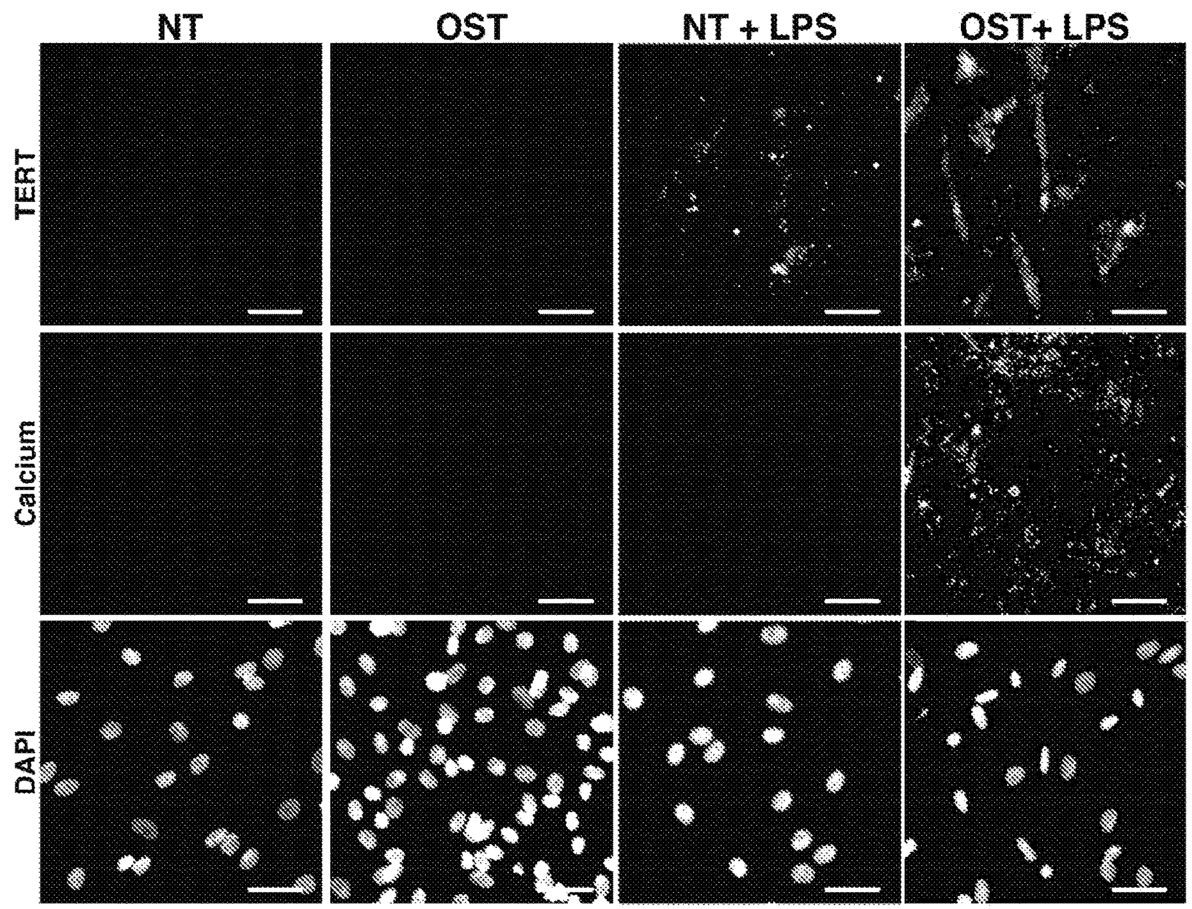
FIG. 14A is a photomicrograph (Scale bar, 50 um)
Figure 14B:
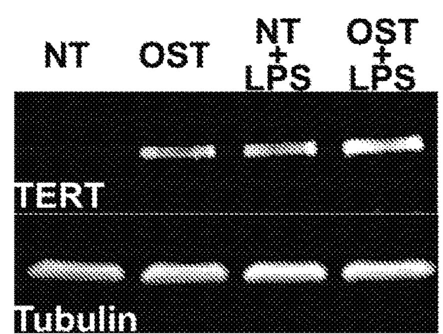
FIG. 14B is a photograph of a western blot, showing that inflammatory stress induces TERT expression and premature calcification.

Inflammatory stress induces TERT expression and premature calcification. hMSCs were cultured under normal growth (NT) or osteogenic (OST) conditions for 11 days with 5 ug/mL exogenous LPS to mimic an inflammatory environment. In FIG. 14A, immunocytochemistry shows OST or LPS alone increases TERT expression. In combination, OST+LPS increases induced premature calcification as compared to OST treatment alone. FIG. 14B shows protein quantification by western blot, which further confirms increased levels of TERT protein in cells treated with OST and LPS alone, and shows a further increase when OST and LPS treatment is combined. Representative images shown of n=3 experiments. Of note, we were not able to detect calcification with OST-alone treatment at this early time-point, indicating that the upregulation of TERT precedes mineralization. This suggests inflammatory pathways as a potential mechanism for the upregulation of TERT in calcified valves, which precedes osteogenesis.

TERT can interact with transcription factors to upregulate gene transcription. Signal transducers and activators of transcription (STAT) proteins mediate inflammatory, proliferative, and apoptotic programs. They function as transcription factors and also recruit histone acetyltransferases (HATs) to upregulate gene transcription. STAT5A and STAT5B (collectively, STAT5) are encoded by two different genes, but 96% of their amino acid sequence is shared. STAT5 was shown to promote the osteogenic differentiation of murine MSCs. Studies in cancer cells identified that STAT proteins, including STAT5, induce TERT gene expression. SMA-α and RUNX2 are markers of the transition of a quiescent VIC to an activated VIC, and these two markers are significantly upregulated in CAVD valve tissues. Next, we tested whether factors known to promote CAVD pathogenesis also increase TERT, and whether knocking down TERT affects expression of genes involved in osteogenesis. Inflammatory stress induces TERT expression and premature calcification. hMSCs were cultured under osteogenic conditions for 11 days with exogenous LPS to mimic an inflammatory environment. STAT5 and TERT were evaluated in osteogenic reprogramming. hMSCs were cultured under normal growth (NT) or osteogenic (OST) conditions for 11 days with 5 ug/mL exogenous LPS to mimic an inflammatory environment. Immunocytochemistry showed that OST or LPS alone increases TERT expression. In combination, OST+LPS increases induced premature calcification as compared to OST treatment alone. Protein quantification by western blot further confirmed increased levels of TERT protein in cells treated with OST and LPS alone, and showed a further increase when OST and LPS treatment is combined. In further work, RUNX2 and SMA-α (ACTA2) are significantly increased in CAVD valve tissue compared to healthy valve tissue. The algorithmic tool LASAGNA was used to identify 27 shared transcription factor binding sites in the 1 kb region upstream of the transcriptional start sites in the human SMA-α and RUNX2 gene promoters. Of the 27 shared transcription factor binding sites in the RUNX2 and SMA-α gene promoters, STAT5 binding sites are the highest scored and most prevalent (FIG. 15A). hMSCs undergoing osteogenic differentiation show increased levels of STAT5 protein. CAVD VICs expressed higher levels of STAT5A and STAT5B mRNA compared to healthy VICs. Regarding FIG. 15A, hMSCs were transiently transduced with scrambled (shCT) or TERT-specific (shTERT) short-hairpin RNA, expressed from a SMARTvector Human TERT Lentiviral shRNA vector, commercially available from Dharmacon of Lafayette Colo.). The TERT shRNA had the sequence: TGCTCAGGTCTTTCTTTTA (SEQ ID NO: 8), which was, used to transiently knockdown TERT expression in hMSCs. Knockdown of TERT was confirmed in these cells and knocking down TERT reduces RUNX2 protein levels (FIG. 15B), suggesting that TERT is necessary for the upregulation of RUNX2 in these cells. Protein lysate was collected 7 days post-transduction and TERT and RUNX2 protein levels quantified. In FIG. 15B, TERT and Runx2 are seen to be decreased in the presence of the shTERT reagent. In further work, co-localization of TERT and STAT5 is seen in the nucleus of CAVD VICs after 28 days of osteogenic stimulation and in valves from CAVD patients. Inflammatory signaling induces TERT expression and accelerates calcification. The transcription factor STAT5 and Runx2 seem to be related to the expression of TERT and calcification.

Genetic deletion of TERT reduces valve calcification in vivo. LDLR knockout and LDLR/TERT double knock out mice were given a high-fat diet for 12 weeks. As shown in FIG. 16, Von Kossa staining on valves from LDLR/TERT double knock out mice after 12 weeks of high fat diet show significantly less calcification than valves from the LDLR knockout mice. Deletion of TERT results in less calcification in the valve.

CONCLUSIONS

- TERT is highly expressed in CAVD valves compared to healthy valves. TERT is present in CAVD VICs, and importantly, healthy VICs upregulate TERT during their switch into a calcifying cell.
- Genetic deletion of TERT inhibits calcification in VSMCs. Though the mechanism is still not clear, our data suggest it is not related to proliferation, senescence, or telomere elongation.
- Inflammatory signaling upregulates TERT in VICs. Also, TERT is related to the activation of osteogenic differentiation through interaction with transcription factors such as STAT5 and RUNX2.
- Preliminary data shows a possible role of TERT in chromatin remodeling during calcification, ligated to the BRG complex.

Example 2—Gene Editing for Introduction of Construct for Expressing TERT Interfering RNA To engineer MSCs such that they will have reduced TERT gene expression, a short-hairpin RNA construct that specifically targets TERT mRNA for degradation (similar to those above from Dharmacon) is introduced into human AAVS1 locus using a kit similar to the AAVS1 Safe Harbor Targeting System from SBI or the Safe Harbor Gene Knock-in Kits from Genecopoeia. The shRNA sequence that targets TERT is cloned into the Multiple Cloning Site of a AAVS1 targeting vector downstream of a constitutively active promoter. Using either CRISPR or TALEN gene editing technology, this construct is packaged into a lentiviral vector to deliver the construct to the cells where it will integrate into the AAVS1 locus. The AAVS1 locus is a well-validated "safe harbor" in the human genome, that was first described in 2011 by Sadelain et al. (*Nat Rev Cancer.* 2011 Dec. 1; 12(1):51-8), thus insertion of an shRNA construct at that site should not cause off-target damage.

Non-limiting aspects or embodiments of the present invention will now be described in the following numbered clauses:

Clause 1. A method of preparing a cardiovascular graft, comprising seeding a bioerodible cell growth scaffold with mesenchymal stem cells (MSCs) that are modified to reduce or eliminate expression or activity of telomerase reverse transcriptase (TERT).

Clause 2. The method of clause 1, further comprising culturing the MSCs on the graft ex vivo.

Clause 3. The method of clause 1 or 2, wherein the mesenchymal stem cells (MSCs) are modified to reduce or eliminate TERT expression.

Clause 4. The method of any one of clauses 1-3, wherein the MSCs are genetically modified, either transiently or permanently, to knock out or to knock down expression of TERT.

Clause 5. The method of any one of clauses 1-4, wherein the MSCs comprise an interfering RNA targeting TERT.

Clause 6. The method of any one of clauses 1-5, wherein the MSCs are genetically modified to express a transgene expressing an interfering RNA, such as a transgene for expressing an shRNA that is processed by Dicer to produce siRNA targeting TERT RNA.

Clause 7. The method of clause 6, wherein the transgene is delivered to the cell in a viral vector.

Clause 8. The method of clause 7, wherein the viral vector is a lentivirus or a gamma-retrovirus vector.

Clause 9. The method of clause 7, wherein the viral vector is an Adeno-Associated Virus vector.

Clause 10. The method of clause 6, wherein the transgene is delivered to the cell by gene editing.

Clause 11. The method of clause 8, wherein the transgene is incorporated into a safe harbor site in the genome of the MSCs.

Clause 12. The method of clause 9, wherein the transgene is incorporated into the AAVS1 site in the genome of the MSCs.

Clause 13. The method of any one of clauses 6-12, wherein the transgene produces an shRNA comprising, or consisting of, the nucleotide sequence TGCTCAGGTCTTTCTTTTA (SEQ ID NO: 8), a sequence having at least 80% or 90% sequence identity to TGCTCAGGTCTTTCTTTTA (SEQ ID NO: 8), or a sequence able to specifically hybridize to the sequence TGCTCAGGTCTTTCTTTTA (SEQ ID NO: 8).

Clause 14. The method of clause 1, wherein the MSCs are human MSCs.

Clause 15. The method of clause 4, wherein TERT is knocked out by gene editing.

Clause 16. The method of clause 4, wherein TERT is knocked out by introduction of a stop codon into its open reading frame.

Clause 17. The method of clause 1, wherein the bioerodible cell growth scaffold or matrix is configured or adapted to replace at least a portion of a heart valve, such as a heart valve, annulus and/or chordae tendineae.

Clause 18. A cardiovascular graft comprising mesenchymal stem cells (MSCs) modified to reduce or eliminate expression or activity of telomerase reverse transcriptase (TERT) or cells differentiated from the modified MSCs modified to reduce or eliminate expression or activity of TERT.

Clause 19. The cardiovascular graft of clause 18, configured as a heart valve, or a portion thereof, such as a heart valve, annulus and/or chordae tendineae.

Clause 20. The cardiovascular graft of clause 18, configured as a prosthetic blood vessel.

Clause 21. The cardiovascular graft of any one of clauses 18-20, comprising a bioerodible cell growth scaffold comprising the modified MSCs.

Clause 22. The cardiovascular graft of any one of clauses 18-21, wherein the MSCs are treated with a TERT interfering RNA, such as a shRNA, to reduce or eliminate expression of TERT in the MSCs.

Clause 23. The cardiovascular graft of any one of clauses 18-22, wherein the MSCs are genetically modified to down-regulate or to delete TERT.

Clause 24. The cardiovascular graft of any one of clauses 18-23, wherein the MSCs are genetically modified to knock out or to knock down expression of TERT.

Clause 25. The cardiovascular graft of any one of clauses 18-24, wherein the MSCs comprise an interfering RNA targeting TERT.

Clause 26. The cardiovascular graft of any one of clauses 18-25, wherein the MSCs are modified to express a transgene expressing an shRNA that is processed by Dicer to produce siRNA targeting TERT RNA.

Clause 27. The cardiovascular graft of clause 26, wherein the transgene is delivered to the cell in a viral vector.

Clause 28. The cardiovascular graft of clause 27, wherein the viral vector is a lentivirus or a gamma-retrovirus vector.

Clause 29. The cardiovascular graft of clause 27, wherein the viral vector is an Adeno-Associated Virus vector.

Clause 30. The cardiovascular graft of clause 26, wherein the transgene is delivered to the cell by gene editing.

Clause 31. The cardiovascular graft of clause 30, wherein the transgene is incorporated into a safe harbor site in the genome of the MSCs.

Clause 32. The cardiovascular graft of clause 31, wherein the transgene is incorporated into the AAVS1 site in the genome of the MSCs.

Clause 33. The cardiovascular graft of clause 24, wherein TERT is knocked out by gene editing.

Clause 34. The cardiovascular graft of clause 24, wherein TERT is knocked out by introduction of a stop codon into its open reading frame.

Clause 35. The cardiovascular graft of any one of clauses 18-34, wherein the MSCs are human MSCs.

Clause 36. A method of treating a cardiovascular defect or injury in a patient, comprising implanting or depositing at a site of a defect or injury in a patient, a cardiovascular graft according to any one of clauses 18-35.

Clause 37. The method of clause 36, wherein the MSCs are autologous to the patient.

Clause 38. The method of clause 36 or 37, wherein the MSCs comprise a TERT interfering RNA to knock down expression of TERT in the MSCs.

Clause 39. The method of any one of clauses 36-38, wherein the MSCs are genetically modified to down-regulate or to delete TERT.

Clause 40. The method of any one of clauses 36-39, wherein the MSCs are human MSCs.

Clause 41. The method of any one of clauses 26-40, wherein the cardiovascular graft is configured as a heart valve, or a portion thereof, such as a heart valve, annulus and/or chordae tendineae.

Clause 42. The method of any one of clauses 36-40, wherein the cardiovascular graft is configured as a prosthetic blood vessel.

The embodiments have been described with reference to various examples. Modifications and alterations will occur to others upon reading and understanding the foregoing examples. Accordingly, the foregoing examples are not to be construed as limiting the disclosure.

What is claimed is:

1. A cardiovascular graft, comprising mesenchymal stem cells (MSCs), modified to reduce or eliminate expression or activity of telomerase reverse transcriptase (TERT) or cells differentiated from the modified MSCs modified to reduce or eliminate expression or activity of TERT, wherein the MSCs are treated with a TERT-interfering RNA to reduce or eliminate expression of TERT in the MSCs, and/or the MSCs are genetically modified to knock out or to knock down expression of TERT.

2. The cardiovascular graft of claim 1, configured as a heart valve, or a portion thereof, annulus and/or chordae tendineae, or as a prosthetic blood vessel.

3. The cardiovascular graft of claim 1, comprising a bioerodible cell growth scaffold comprising the modified MSCs.

4. The cardiovascular graft of claim 1, wherein the MSCs are treated with a TERT interfering RNA, to reduce or eliminate expression of TERT in the MSCs.

5. The cardiovascular graft of claim 1, wherein the MSCs are genetically modified to knock out or to knock down expression of TERT.

6. The cardiovascular graft of claim 5, wherein the MSCs are modified to express a transgene expressing an interfering RNA targeting TERT RNA.

7. The cardiovascular graft of claim 6, wherein the transgene is delivered to the cell by gene editing, optionally into a safe harbor site in the genome of the MSCs.

8. The cardiovascular graft of claim 5, wherein TERT is knocked out by gene editing.

9. A method of preparing a cardiovascular graft, comprising seeding a bioerodible cell growth scaffold with mesenchymal stem cells (MSCs) that are modified to reduce or eliminate expression or activity of telomerase reverse transcriptase (TERT), wherein the MSCs are treated with a TERT-interfering RNA to reduce or eliminate expression of TERT in the MSCs, and/or the MSCs are genetically modified to knock out or to knock down expression of TERT.

10. The method of claim 9, further comprising culturing the MSCs on the graft ex vivo.

11. The method of claim 9, wherein the mesenchymal stem cells (MSCs) are genetically modified, either transiently or permanently, to knock out or to knock down expression of TERT.

12. The method of claim 9, wherein the MSCs comprise an interfering RNA targeting TERT.

13. The method of claim 9, wherein the MSCs are genetically modified to express a transgene for expressing an interfering RNA targeting TERT RNA.

14. The method of claim 13, wherein the transgene is delivered to the cell by gene editing, and optionally into a safe harbor site in the genome of the MSCs.

15. The method of claim 13, wherein the transgene produces an shRNA comprising, or consisting of, the nucleotide sequence TGCTCAGGTCTTTCTTTTA (SEQ ID NO: 8), a sequence having at least 80% or 90% sequence identity to TGCTCAGGTCTTTCTTTTA (SEQ ID NO: 8), or a sequence able to specifically hybridize to the sequence TGCTCAGGTCTTTCTTTTA (SEQ ID NO: 8).

16. The method of claim 11, wherein TERT is knocked out by gene editing.

17. The method of claim 9, wherein the bioerodible cell growth scaffold or matrix is configured or adapted to replace at least a portion of a heart valve, annulus and/or chordae tendineae.

18. A method of treating a cardiovascular defect or injury in a patient, comprising implanting or depositing at a site of a defect or injury in a patient a cardiovascular graft comprising mesenchymal stem cells (MSCs), modified to reduce or eliminate expression or activity of telomerase reverse transcriptase (TERT) or cells differentiated from the modified MSCs modified to reduce or eliminate expression or activity of TERT, wherein the MSCs are treated with a TERT-interfering RNA to reduce or eliminate expression of TERT in the MSCs, and/or the MSCs are genetically modified to knock out or to knock down expression of TERT.

19. The method of claim 18, wherein the MSCs are autologous to the patient.

20. The method of claim 18, wherein the MSCs comprise a TERT interfering RNA to knock down expression of TERT in the MSCs.

21. The method of claim 18, wherein the MSCs are genetically modified to down-regulate or to delete TERT.

22. The method of claim 18, wherein the cardiovascular graft is configured as a heart valve, or a portion thereof, annulus and/or chordae tendineae, or as a prosthetic blood vessel.

* * * * *